US008067669B2

(12) United States Patent
English et al.

(10) Patent No.: US 8,067,669 B2
(45) Date of Patent: Nov. 29, 2011

(54) METHOD FOR INDUCING RESISTANCE TO FUNGAL INFECTION IN TRANSGENIC PLANTS USING PLANT DEFENSE PEPTIDES

(75) Inventors: James T. English, Columbia, MO (US); Francis J. Schmidt, Columbia, MO (US); Gary Stacey, Columbia, MO (US); Zhiwei Fang, Columbia, MO (US)

(73) Assignee: The Curators Of The University Of Missouri, Columbia, MO (US)

( * ) Notice: Subject to any disclaimer, the term of this patent is extended or adjusted under 35 U.S.C. 154(b) by 0 days.

(21) Appl. No.: 12/718,709

(22) Filed: Mar. 5, 2010

(65) Prior Publication Data

US 2010/0333238 A1 Dec. 30, 2010

Related U.S. Application Data

(60) Division of application No. 11/498,969, filed on Aug. 2, 2006, now Pat. No. 7,700,831, and a continuation-in-part of application No. 09/829,549, filed on Apr. 10, 2001, now abandoned.

(60) Provisional application No. 60/704,933, filed on Aug. 2, 2005, provisional application No. 60/195,785, filed on Apr. 10, 2000.

(51) Int. Cl.

| | |
|---|---|
| ***A01H 1/00*** | (2006.01) |
| ***C12N 15/09*** | (2006.01) |
| ***C12N 15/82*** | (2006.01) |
| ***C12N 15/31*** | (2006.01) |

(52) U.S. Cl. ........ 800/279; 800/278; 800/298; 800/312; 435/320.1; 536/23.1; 536/23.4; 536/23.7

(58) Field of Classification Search ........................ None
See application file for complete search history.

(56) References Cited

U.S. PATENT DOCUMENTS

| | | | |
|---|---|---|---|
| 4,458,066 | A | 7/1984 | Caruthers et al. |
| 4,973,679 | A | 11/1990 | Caruthers et al. |
| 6,235,974 | B1 | 5/2001 | Qiu et al. |
| 6,420,110 | B1 | 7/2002 | Gyuris et al. |
| 7,018,801 | B2 | 3/2006 | Kodadek |
| 2001/0029024 | A1 | 10/2001 | Kodadek |

FOREIGN PATENT DOCUMENTS

| | | |
|---|---|---|
| WO | WO 99/51780 | 10/1999 |

OTHER PUBLICATIONS

U.S. Appl. No. 09/829,549, filed Apr. 10, 2001.*
U.S. Appl. No. 11/498,969, filed Aug. 2, 2006.*
Rudi Glockshuber, et al., A Comparison of Strategies to Stabilize Immunoglobulin F-Fragments, pp. 1362-1367, Biochemistry, 1990.
PCT/US06/30291 International Search Report and Written Opinion mailed Sep. 19, 2008, 12 pages.
Petrenko, V.A. et al. "A library of organic landscapes on filamentous phage" Protein Engineering, vol. 9 No. 9, 1996, pp. 797-801.
Gough, K.C. et al. "Selection of phage antibodies to surface epitopes of *Phytophthora infestans*", J. of Immun. Methods, 228 (1999) 97-108.

* cited by examiner

*Primary Examiner* — Medina A Ibrahim
(74) *Attorney, Agent, or Firm* — Lathrop & Gage LLP

(57) ABSTRACT

A method for the identification of peptides having an affinity for the surface of fungi is provided as is a method for the identification of peptides capable of affecting the development of a fungus. Also provided are compositions comprising peptides identified using the method of the present invention. In addition, isolated polynucleotides, vectors, expression cassettes and transformed cells capable of expressing peptides identified by the method of the present invention are provided. Such polynucleotides, vectors, expression cassettes may be introduced into and confer upon plants the capability to resist fungal infection.

14 Claims, 8 Drawing Sheets

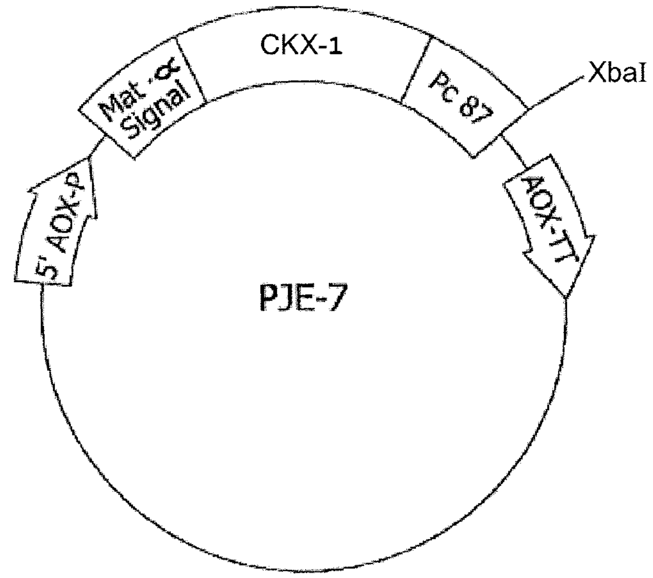

5' AG CTA GCA GAT AGA CCA TCA ATG TCA CCA ACA TAG T 3'
3' T CGT CTA TCT GGT AGT TAC AGT GGT TGT ATC AGA TC 5'

FIG. 6

```
MRFPSIFTAV  LFAASSALAA  PVNTTTEDET  AQIPADAVIG  YSDLEGDFDV
AVLPFSNSTN  NGLLFINTTI  ASIAAKEEGV  SLEKRLAAGT  PALGDDRGRP
WPASLAALAL  DGKLRTDSNA  TAAASTDFGN  ITSALPAAVL  YPSTGDLVAL
LSAANSTPGW  PYTIAFRGRG  HSLMGQAFAP  GGVVVNMASL  GDAAAPPRIN
VSADGRYVDA  GGEQVWIDVL  RASLARGVAP  RSWNDYLYLT  VGGTLSNAGI
SGQAFRHGPQ  ISNVLEMDVT  TGHGEMVTCS  KQLNADLFDA  VLGGLGQFGV
ITRARIAVEP  APARARWVRF  VYTDFAAFSA  DQERLTAPRP  GGGGASFGPM
SYVEGSVFVN  QSLATDLANT  GFFTDADVAR  IVALAGERNA  TTVYSIEATL
NYDNATAAAA  AVDQELASVL  GTLSYVEGFA  FQRDVAYAAF  LDRVHGEEVA
LNKLGLWRVP  HPWLNMFVPR  SRIADFDRGV  FKGILQGTDI  VGPLIVYPLN
KSMWDDGMSA  ATPSEDVFYA  VSLLFSSVAP  NDLARLQEQN  RRILRFCDLA
GIQYKTYLAR  HTDRSDWVRH  FGAAKWNRFV  EMKNKYDPKR  LLSPGQDIFN
KLADRPSMSP  T
```

FIG. 7

SEQUENCE LISTING

<160> NUMBER OF SEQ ID NOS: 63

<210> SEQ ID NO 1
<211> LENGTH: 33
<212> TYPE: PRT
<213> ORGANISM: Filamentous bacteriophage
<220> FEATURE:
<221> NAME/KEY: VARIANT
<222> LOCATION: (9)..(23)
<223> OTHER INFORMATION: X is any amino acid encoded by the codon NNK
where N is A, T, C, or G; and K designates G or T.

<400> SEQUENCE: 1

```
Leu Val Pro Met Leu Ser Phe Ala Xaa Xaa Xaa Xaa Xaa Xaa Xaa Xaa
1               5                   10                  15

Xaa Xaa Xaa Xaa Xaa Xaa Xaa Pro Ala Glu Gly Asp Asp Pro Ala Lys
            20                  25                  30

Ala
```

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: Synthetic Construct

<400> SEQUENCE: 2
ggagccttta attgtatcgg 20

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
agtagcagaa gcctgaaga 19

<210> SEQ ID NO 4
<211> LENGTH: 9
<212> TYPE: PRT
<213> ORGANISM: Artificial Sequence
<220> FEATURE:
<223> OTHER INFORMATION: Random peptide insert

<400> SEQUENCE: 4

```
Ala Ala Pro Asp Leu Gln Asp Ala Met
1               5
```

<210> SEQ ID NO 5
<211> LENGTH: 9
<212> TYPE: PRT
<213> ORGANISM: Artificial Sequence
<220> FEATURE:
<223> OTHER INFORMATION: Random peptide insert

<400> SEQUENCE: 5

```
Ala Asp Arg Leu Asn Ser Asp Ala Gly
1               5
```

<210> SEQ ID NO 6
<211> LENGTH: 9
<212> TYPE: PRT
<213> ORGANISM: Artificial Sequence
<220> FEATURE:
<223> OTHER INFORMATION: Random peptide insert

<400> SEQUENCE: 6

Ala Asp Arg Pro Ser Thr Thr Ser Leu
1               5

<210> SEQ ID NO 7
<211> LENGTH: 9
<212> TYPE: PRT
<213> ORGANISM: Artificial Sequence
<220> FEATURE:
<223> OTHER INFORMATION: Random peptide insert

<400> SEQUENCE: 7

Ala Asp Pro Pro Arg Thr Val Ser Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Random peptide insert

<400> SEQUENCE: 8

Ala Asp Arg Pro Ser Met Ser Pro Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Random peptide insert

<400> SEQUENCE: 9

Ala Asp Arg Thr Ser Asn Ala Ser Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Random peptide insert

<400> SEQUENCE: 10

Ala Asp Lys Ser Tyr Ile Pro Ser Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Random peptide insert

<400> SEQUENCE: 11

Ala Val Arg Asn Pro Ser His His Ser
1               5

<210> SEQ ID NO 12
<211> LENGTH: 9

<212> TYPE: PRT
<213> ORGANISM: Artificial Sequence
<220> FEATURE:
<223> OTHER INFORMATION: Random peptide insert

<400> SEQUENCE: 12

Ala Asp Pro Thr Pro Arg Gly His Ser
1 5

<210> SEQ ID NO 13
<211> LENGTH: 9
<212> TYPE: PRT
<213> ORGANISM: Artificial Sequence
<220> FEATURE:
<223> OTHER INFORMATION: Random peptide insert

<400> SEQUENCE: 13

Ala Asp Pro Thr Arg Gln Pro His Ser
1 5

<210> SEQ ID NO 14
<211> LENGTH: 9
<212> TYPE: PRT
<213> ORGANISM: Artificial Sequence
<220> FEATURE:
<223> OTHER INFORMATION: Random peptide insert

<400> SEQUENCE: 14

Ala Glu His Gln Asn Ser Ala Gly Pro
1 5

<210> SEQ ID NO 15
<211> LENGTH: 10
<212> TYPE: PRT
<213> ORGANISM: Artificial Sequence
<220> FEATURE:
<223> OTHER INFORMATION: Random peptide insert

<400> SEQUENCE: 15

Ala Asp Ala Arg Ser Ala Gly Ala Ile Ser
1 5 10

<210> SEQ ID NO 16
<211> LENGTH: 9
<212> TYPE: PRT
<213> ORGANISM: Artificial Sequence
<220> FEATURE:
<223> OTHER INFORMATION: Random peptide insert

<400> SEQUENCE: 16

Ala Asp Ser Lys Asn Ala Gly Pro Met
1 5

<210> SEQ ID NO 17
<211> LENGTH: 9
<212> TYPE: PRT
<213> ORGANISM: Artificial Sequence
<220> FEATURE:
<223> OTHER INFORMATION: Random peptide insert

<400> SEQUENCE: 17

Ala Glu Thr Lys Phe Ser Gly Ser Ala
1 5

<210> SEQ ID NO 18
<211> LENGTH: 9
<212> TYPE: PRT
<213> ORGANISM: Artificial Sequence
<220> FEATURE:
<223> OTHER INFORMATION: Random peptide insert

<400> SEQUENCE: 18

Ala Asp Pro Lys Gly Ser Gly Val Thr
1 5

<210> SEQ ID NO 19
<211> LENGTH: 9
<212> TYPE: PRT
<213> ORGANISM: Artificial Sequence
<220> FEATURE:
<223> OTHER INFORMATION: Random peptide insert

<400> SEQUENCE: 19

Ala Gly Leu Thr Ser Pro Asn Asp Met
1 5

<210> SEQ ID NO 20
<211> LENGTH: 9
<212> TYPE: PRT
<213> ORGANISM: Artificial Sequence
<220> FEATURE:
<223> OTHER INFORMATION: Random peptide insert

<400> SEQUENCE: 20

Ala Asp Ile Thr Asp Pro Met Gly Ala
1 5

<210> SEQ ID NO 21
<211> LENGTH: 9
<212> TYPE: PRT
<213> ORGANISM: Artificial Sequence
<220> FEATURE:
<223> OTHER INFORMATION: Random peptide insert

<400> SEQUENCE: 21

Ala Val Gly Thr His Thr Pro Asp Ser
1 5

<210> SEQ ID NO 22
<211> LENGTH: 9
<212> TYPE: PRT
<213> ORGANISM: Artificial Sequence
<220> FEATURE:
<223> OTHER INFORMATION: Random peptide insert

<400> SEQUENCE: 22

Ala Val Ser Pro Asn Val His Asp Gly
1 5

<210> SEQ ID NO 23
<211> LENGTH: 15
<212> TYPE: PRT
<213> ORGANISM: Artificial Sequence
<220> FEATURE:
<223> OTHER INFORMATION: Random peptide insert

<400> SEQUENCE: 23

Val Ala Ala Phe Ser Leu Val Trp Ala Thr His Leu Met Leu Ser
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Random peptide insert

<400> SEQUENCE: 24

Leu Thr Arg Cys Leu Val Ser Thr Glu Met Ala Ala Arg Arg Pro
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Random peptide insert

<400> SEQUENCE: 25

Ser Ala Pro Tyr Leu Pro Tyr Phe Asp Leu Leu His Phe Pro Ile
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (14)..(14)
<223> OTHER INFORMATION: x=unknown amino acid

<400> SEQUENCE: 26

Pro Ser Ser Tyr Glu Ala Ser Arg Arg Pro Glu His Trp Xaa Phe
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: Random peptide insert

<400> SEQUENCE: 27

Ser Ala Thr Asp Thr Thr Leu Pro Met Met Thr Ala Ile Arg Ser
1 5 10 15

<210> SEQ ID NO 28
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (9)..(9)
<223> OTHER INFORMATION: x = unknown amino acid

<400> SEQUENCE: 28

Thr Arg Leu Ser Pro Met Glu Ser Xaa Ala Met Leu Leu Ala Pro
1 5 10 15

<210> SEQ ID NO 29
<211> LENGTH: 15
<212> TYPE: PRT
<213> ORGANISM: Artificial Sequence
<220> FEATURE:
<223> OTHER INFORMATION: Random peptide insert

<400> SEQUENCE: 29

Leu Leu Pro Val Ser Pro Pro Phe Ala Pro Asn Ala Ser Ser Thr
1 5 10 15

<210> SEQ ID NO 30
<211> LENGTH: 15
<212> TYPE: PRT
<213> ORGANISM: Artificial Sequence
<220> FEATURE:
<223> OTHER INFORMATION: Random peptide insert

<400> SEQUENCE: 30

Met Ser Asn Phe Pro Thr Ser His Ala Pro Cys Pro Val Glu Ile
1 5 10 15

<210> SEQ ID NO 31
<211> LENGTH: 15
<212> TYPE: PRT
<213> ORGANISM: Artificial Sequence
<220> FEATURE:
<223> OTHER INFORMATION: Random peptide insert

<400> SEQUENCE: 31

Glu Phe Arg Lys Asn Tyr Pro Ser Ala Ala Pro Leu Ile Pro Arg
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (2)..(2)
<223> OTHER INFORMATION: x = unknown amino acid

<400> SEQUENCE: 32

Pro Xaa Val His Gly Ser Ile Pro Leu Thr Pro Pro Leu Gly Phe
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (3)..(3)
<223> OTHER INFORMATION: x =unknown amino acid

<400> SEQUENCE: 33

Leu Phe Xaa Cys Tyr Pro Pro Cys Thr Tyr Ser Tyr Cys Leu Ser
1 5 10 15

<210> SEQ ID NO 34
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (14)..(14)
<223> OTHER INFORMATION: x = unknown amino acid

<400> SEQUENCE: 34

Met Ser Asn Phe Pro Thr Ser His Ala Pro Cys Pro Val Xaa Ile
1 5 10 15

<210> SEQ ID NO 35
<211> LENGTH: 15
<212> TYPE: PRT

<213> ORGANISM: Artificial Sequence
<220> FEATURE:
<223> OTHER INFORMATION: Random peptide insert

<400> SEQUENCE: 35

Pro Glu Trp Lys Ser Ser Trp Ser Pro Cys Thr Pro Arg Cys Pro
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (11)..(11)
<223> OTHER INFORMATION: x is M or I

<400> SEQUENCE: 36

Ala Met Ser Arg Trp Leu Arg Pro Arg Glu Xaa Asn Ala Pro Pro
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (6)..(6)
<223> OTHER INFORMATION: x = unknown amino acid
<220> FEATURE:
<221> NAME/KEY: VARIANT
<222> LOCATION: (10)..(10)
<223> OTHER INFORMATION: x = unknown amino acid

<400> SEQUENCE: 37

Thr His Thr Thr Phe Xaa Val Thr Val Xaa Leu His Glu Pro Pro
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (6)..(6)
<223> OTHER INFORMATION: x = unknown amino acid
<220> FEATURE:
<221> NAME/KEY: VARIANT
<222> LOCATION: (10)..(10)
<223> OTHER INFORMATION: x = unknown amino acid

<400> SEQUENCE: 38

Thr His Thr Thr Phe Xaa Val Thr Val Xaa Leu His Glu Pro Pro
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: Random peptide insert

<400> SEQUENCE: 39

Pro Thr Leu Gly Arg Phe Asn Arg Pro Ser Cys Ser Ile Ile Val
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Random peptide insert

<400> SEQUENCE: 40

Ala Pro Gln Cys His Pro His Leu Pro Phe Asp Met Ile His Val
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Random peptide insert
<220> FEATURE:
<221> NAME/KEY: VARIANT
<222> LOCATION: (12)..(12)
<223> OTHER INFORMATION: x = unknown amino acid

<400> SEQUENCE: 41

Asn His Asn Ser Leu Pro Ala Gln Tyr Leu Val Xaa Ile Leu Arg
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Random peptide insert

<400> SEQUENCE: 42

Asp Gln Pro Cys Thr Pro Ser Pro Asp Val Ser Phe Tyr Arg Ser
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Random peptide insert

<400> SEQUENCE: 43

Val Ala Ala Pro Ser His Trp Leu Lys Pro Ser Leu Asp Cys Phe
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Random peptide insert

<400> SEQUENCE: 44

Asn Pro Leu Tyr Lys Asn Pro Pro Pro Arg Val Ala Met Cys Leu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Random peptide insert

<400> SEQUENCE: 45

-continued

```
Leu Ile Phe Arg Tyr Ala Pro Pro Pro Leu Phe Leu Arg Pro Pro
1               5                   10                  15


<210> SEQ ID NO 46
<211> LENGTH: 36
<212> TYPE: DNA
<213> ORGANISM: Artificial Sequence
<220> FEATURE:
<223> OTHER INFORMATION: + Strand of DNA encoding peptide Pc 87

<400> SEQUENCE: 46

agctagcaga tagaccatca atgtcaccaa catagt                              36


<210> SEQ ID NO 47
<211> LENGTH: 36
<212> TYPE: DNA
<213> ORGANISM: Artificial Sequence
<220> FEATURE:
<223> OTHER INFORMATION: - strand of DNA encoding peptide Pc 87

<400> SEQUENCE: 47

ctagactatg ttggtgacat tgatggtcta tctgct                              36


<210> SEQ ID NO 48
<211> LENGTH: 611
<212> TYPE: PRT
<213> ORGANISM: Artificial Sequence
<220> FEATURE:
<223> OTHER INFORMATION: Random peptide Pc 87
<220> FEATURE:
<221> NAME/KEY: SIGNAL
<222> LOCATION: (1)..(1)
<223> OTHER INFORMATION: Mat-alpha secretory sequence
<220> FEATURE:
<221> NAME/KEY: DOMAIN
<222> LOCATION: (1)..(1)
<223> OTHER INFORMATION: Cytokinin oxidase 1
<220> FEATURE:
<221> NAME/KEY: DOMAIN
<222> LOCATION: (1)..(1)
<223> OTHER INFORMATION: Linker
<220> FEATURE:
<221> NAME/KEY: DOMAIN
<222> LOCATION: (1)..(1)
<223> OTHER INFORMATION: Random peptide Pc 87

<400> SEQUENCE: 48

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Asp Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Leu Ala Ala Gly Thr Pro Ala Leu Gly Asp Asp
                85                  90                  95

Arg Gly Arg Pro Trp Pro Ala Ser Leu Ala Ala Leu Ala Leu Asp Gly
            100                 105                 110

Lys Leu Arg Thr Asp Ser Asn Ala Thr Ala Ala Ala Ser Thr Asp Phe
        115                 120                 125

Gly Asn Ile Thr Ser Ala Leu Pro Ala Ala Val Leu Tyr Pro Ser Thr
    130                 135                 140
```

-continued

```
Gly Asp Leu Val Ala Leu Leu Ser Ala Ala Asn Ser Thr Pro Gly Trp
145                 150                 155                 160

Pro Tyr Thr Ile Ala Phe Arg Gly Arg Gly His Ser Leu Met Gly Gln
                165                 170                 175

Ala Phe Ala Pro Gly Gly Val Val Val Asn Met Ala Ser Leu Gly Asp
            180                 185                 190

Ala Ala Ala Pro Pro Arg Ile Asn Val Ser Ala Asp Gly Arg Tyr Val
        195                 200                 205

Asp Ala Gly Gly Glu Gln Val Trp Ile Asp Val Leu Arg Ala Ser Leu
    210                 215                 220

Ala Arg Gly Val Ala Pro Arg Ser Trp Asn Asp Tyr Leu Tyr Leu Thr
225                 230                 235                 240

Val Gly Gly Thr Leu Ser Asn Ala Gly Ile Ser Gly Gln Ala Phe Arg
                245                 250                 255

His Gly Pro Gln Ile Ser Asn Val Leu Glu Met Asp Val Ile Thr Gly
            260                 265                 270

His Gly Glu Met Val Thr Cys Ser Lys Gln Leu Asn Ala Asp Leu Phe
        275                 280                 285

Asp Ala Val Leu Gly Gly Leu Gly Gln Phe Gly Val Ile Thr Arg Ala
    290                 295                 300

Arg Ile Ala Val Glu Pro Ala Pro Ala Arg Ala Arg Trp Val Arg Phe
305                 310                 315                 320

Val Tyr Thr Asp Phe Ala Ala Phe Ser Ala Asp Gln Glu Arg Leu Thr
                325                 330                 335

Ala Pro Arg Pro Gly Gly Gly Gly Ala Ser Phe Gly Pro Met Ser Tyr
            340                 345                 350

Val Glu Gly Ser Val Phe Val Asn Gln Ser Leu Ala Thr Asp Leu Ala
        355                 360                 365

Asn Thr Gly Phe Phe Thr Asp Ala Asp Val Ala Arg Ile Val Ala Leu
    370                 375                 380

Ala Gly Glu Arg Asn Ala Thr Thr Val Tyr Ser Ile Glu Ala Thr Leu
385                 390                 395                 400

Asn Tyr Asp Asn Ala Thr Ala Ala Ala Ala Ala Val Asp Gln Glu Leu
                405                 410                 415

Ala Ser Val Leu Gly Thr Leu Ser Tyr Val Glu Gly Phe Ala Phe Gln
            420                 425                 430

Arg Asp Val Ala Tyr Ala Ala Phe Leu Asp Arg Val His Gly Glu Glu
        435                 440                 445

Val Ala Leu Asn Lys Leu Gly Leu Trp Arg Val Pro His Pro Trp Leu
    450                 455                 460

Asn Met Phe Val Pro Arg Ser Arg Ile Ala Asp Phe Asp Arg Gly Val
465                 470                 475                 480

Phe Lys Gly Ile Leu Gln Gly Thr Asp Ile Val Gly Pro Leu Ile Val
                485                 490                 495

Tyr Pro Leu Asn Lys Ser Met Trp Asp Asp Gly Met Ser Ala Ala Thr
            500                 505                 510

Pro Ser Glu Asp Val Phe Tyr Ala Val Ser Leu Leu Phe Ser Ser Val
        515                 520                 525

Ala Pro Asn Asp Leu Ala Arg Leu Gln Glu Gln Asn Arg Arg Ile Leu
    530                 535                 540

Arg Phe Cys Asp Leu Ala Gly Ile Gln Tyr Lys Thr Tyr Leu Ala Arg
545                 550                 555                 560

His Thr Asp Arg Ser Asp Trp Val Arg His Phe Gly Ala Ala Lys Trp
                565                 570                 575
```

Asn Arg Phe Val Glu Met Lys Asn Lys Tyr Asp Pro Lys Arg Leu Leu
580 585 590

Ser Pro Gly Gln Asp Ile Phe Asn Lys Leu Ala Asp Arg Pro Ser Met
595 600 605

Ser Pro Thr
610

<210> SEQ ID NO 49
<211> LENGTH: 15
<212> TYPE: PRT
<213> ORGANISM: Artificial Sequence
<220> FEATURE:
<223> OTHER INFORMATION: Random peptide insert

<400> SEQUENCE: 49

Ala Asp Pro Cys His Met Pro Pro Arg Met Pro Pro Leu Pro Ile
1 5 10 15

<210> SEQ ID NO 50
<211> LENGTH: 15
<212> TYPE: PRT
<213> ORGANISM: Artificial Sequence
<220> FEATURE:
<223> OTHER INFORMATION: Random peptide insert

<400> SEQUENCE: 50

Asn His Val Ser Thr Leu Lys Thr Arg His Arg Leu Ile Pro Phe
1 5 10 15

<210> SEQ ID NO 51
<211> LENGTH: 15
<212> TYPE: PRT
<213> ORGANISM: Artificial Sequence
<220> FEATURE:
<223> OTHER INFORMATION: Random peptide insert

<400> SEQUENCE: 51

Ser Ser Asn Ala Pro Pro Leu Ser Tyr Pro Pro Leu Leu Val Pro
1 5 10 15

<210> SEQ ID NO 52
<211> LENGTH: 15
<212> TYPE: PRT
<213> ORGANISM: Artificial Sequence
<220> FEATURE:
<223> OTHER INFORMATION: Random peptide insert

<400> SEQUENCE: 52

Thr Met Ala Arg Pro Ile Pro Thr Phe Leu Pro Pro Pro Ser Leu
1 5 10 15

<210> SEQ ID NO 53
<211> LENGTH: 15
<212> TYPE: PRT
<213> ORGANISM: Artificial Sequence
<220> FEATURE:
<223> OTHER INFORMATION: Random peptide insert

<400> SEQUENCE: 53

Thr Val Ala Pro Thr Thr His Arg His Tyr Val Trp Ser Met Asp
1 5 10 15

<210> SEQ ID NO 54
<211> LENGTH: 15
<212> TYPE: PRT
<213> ORGANISM: Artificial Sequence
<220> FEATURE:
<223> OTHER INFORMATION: Random peptide insert

<400> SEQUENCE: 54

Val Phe Thr Pro Met Asn Leu Ser Pro Pro Phe Met Gln Pro Pro
1 5 10 15

<210> SEQ ID NO 55
<211> LENGTH: 15
<212> TYPE: PRT
<213> ORGANISM: Artificial Sequence
<220> FEATURE:
<223> OTHER INFORMATION: Random peptide insert

<400> SEQUENCE: 55

Ala Ala Gly Pro Asn Ile Pro Pro Pro His Arg Ala Ser Thr Trp
1 5 10 15

<210> SEQ ID NO 56
<211> LENGTH: 15
<212> TYPE: PRT
<213> ORGANISM: Artificial Sequence
<220> FEATURE:
<223> OTHER INFORMATION: Random peptide insert

<400> SEQUENCE: 56

Ala His Leu Tyr Ser Gly Ala Ser Leu Tyr Arg Val Tyr Arg Ser
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: Random peptide insert

<400> SEQUENCE: 57

Gly Pro Pro Ser Ile Leu Leu Ala Ile Gly Thr Leu Ser Leu Thr
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: Random peptide insert

<400> SEQUENCE: 58

Leu Ser Ser Pro Tyr Ala Cys Ala Leu Phe Val Val Lys Gly Ala
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: Random peptide insert

<400> SEQUENCE: 59

Arg Gly Trp Ser Val Ser His His Ser Leu Leu Met Pro Val Pro
1 5 10 15

<210> SEQ ID NO 60
<211> LENGTH: 15
<212> TYPE: PRT
<213> ORGANISM: Artificial Sequence
<220> FEATURE:
<223> OTHER INFORMATION: Random peptide insert -continued

```
<400> SEQUENCE: 60

Arg Ser Thr Ala Ser Pro Gln Ala Leu Asn Pro Leu Val Ala Ser
1               5                   10                  15


<210> SEQ ID NO 61
<211> LENGTH: 15
<212> TYPE: PRT
<213> ORGANISM: Artificial Sequence
<220> FEATURE:
<223> OTHER INFORMATION: Random peptide insert

<400> SEQUENCE: 61

Ser Leu Phe Phe Glu Val Ser Arg Met Leu Val Arg Leu Leu Ser
1               5                   10                  15


<210> SEQ ID NO 62
<211> LENGTH: 15
<212> TYPE: PRT
<213> ORGANISM: Artificial Sequence
<220> FEATURE:
<223> OTHER INFORMATION: Random peptide insert

<400> SEQUENCE: 62

Ser Arg Trp Trp Arg Cys Val Thr Met Thr Gln Pro Cys Thr Thr
1               5                   10                  15


<210> SEQ ID NO 63
<211> LENGTH: 15
<212> TYPE: PRT
<213> ORGANISM: Artificial Sequence
<220> FEATURE:
<223> OTHER INFORMATION: Random peptide insert

<400> SEQUENCE: 63

Val Val Ala Leu Arg Trp Gly Trp Ser Pro Leu Arg Pro Pro Gly
1               5                   10                  15
```

METHOD FOR INDUCING RESISTANCE TO FUNGAL INFECTION IN TRANSGENIC PLANTS USING PLANT DEFENSE PEPTIDES

RELATED APPLICATIONS

This application is a divisional application of U.S. application Ser. No. 11/498,969 filed Aug. 2, 2006, now issued as U.S. Pat. No. 7,700,831, which claims benefit of priority to U.S. Provisional Patent Application Ser. No. 60/704,933, filed Aug. 2, 2005, and is a continuation-in-part of U.S. patent application Ser. No. 09/829,549 filed Apr. 10, 2001, now abandoned, which claims benefit of priority to U.S. Provisional Patent Application Ser. No. 60/195,785, filed Apr. 10, 2000. All of the aforementioned applications are herein incorporated by reference.

SEQUENCE LISTING

This application is accompanied by a sequence listing in a computer readable form that accurately reproduces the sequences described herein.

BACKGROUND

This disclosure relates to the use of phage display technology to identify peptides that bind to pathogenic fungi and more particularly to pathogenic fungi of the genera *Phytophthora, Phakapsora*, and *Uromyces*. Random peptide phage display libraries are constructed using degenerate oligonucleotides. Phage expressing the peptides on their surface are contacted with fungi at different life stages and those phage that bind are isolated, amplified and the peptides identified. Once identified, peptides can be screened for anti fungal activity and used to identify and characterize binding sites on fungi.

*Phytophthora* is an economically important disease causing organism in the United States causing large losses in many agronomically important crop species. *Phytophthora sojae* is the second most important pathogen of soybeans in the United States. (Doupnik, *Plant Dis.* 77:1170-1171, 1993). *Phytophthora capsici* has a broad host range and most notably limits production of high-value, solanaceous vegetable crops. Control of these pathogens is particularly difficult, often requiring treatment of entire fields with biocidal compounds. Although effective, increasing concern about the environmental and economic costs of such treatments require the need for alternative control methods.

*Phytophthora* species are obligate parasites adapted to long-term survival in soil in the absence of host plants. Oospores or chlamydospores exist in low densities in the soil and enable survival of the pathogen. In the presence of a susceptible plant, the pathogen progresses rapidly through a series of finely tuned developmental steps that produce cycles of infection and disease. Pathogen development from oospores or chlamydospores through zoospore release, encystment, germination and infection appear straight-forward at first glance. Yet, the procession of life stages is finely tuned to environmental signals, particularly those signals coming from a host plant.

Zoospores are the life-stage of greatest importance for dispersal to root infection sites. A major susceptible site is located just behind the apical meristem of the root where cells are elongating. Exudates released from elongating cells serve as signals that direct chemotactic movement of zoospores toward the site (Carlile, in *Phytophthora: Its Biology, Taxonomy, Ecology and Pathology*, Erwin et al., eds., APS Press, 1983; Deacon and Donaldson, *Mycol. Res.* 97:1153-1171, 1993). The zoospore chemotactic response varies with the composition of root exudates and is species specific. For example, zoospores of *P. capsici, P. cactorum*, and other species are attracted to an array of sugars and amino acids (Hickman, *Phytopathology,* 60:1128-1135, 1970; Khew and Zentmyer, *Phytopathology,* 63:1511-1517, 1973), but zoospores of *P. sojae* are attracted to specific isoflavonoid compounds (Norris et al., *Plant Physiol.,* 117:1171-1178, 1998). Although the precise mechanism of chemoattraction is not known, Deacon and Donaldson (*Mycol. Res.,* 97:1153-1171, 1993) and Carlile (in *Phytophthora: Its Biology, Taxonomy, Ecology and Pathology*, Erwin et al., eds., APS Press, 1983) summarized experiments that suggested the involvement of chemoreceptors on the zoospore surface.

Zoospores encyst as they approach the root surface in response to environmental signals. Encystment of zoospores of *P. palmivora* and other Phytophthora species, for example, can be influenced by local calcium ion concentrations (Griffith et al., *Arch. Microbiol.,* 149:565-571, 1988; Warburton and Deacon, *Fungal Genetics Biol.,* 25:54-62, 1998). Encystment can also be induced by high concentration of chemoattractants or by root cell wall components. For example, zoospores of *P. sojae* encyst in the presence of high concentrations of soybean isoflavonoid compounds (Morris and Ward, *Physiol. Mol. Plant Pathol.,* 40:17-22, 1992). In contrast, zoospores of *Pythium aphanidermatum* encysted when in contact with fucosyl and galactosyl residues from cell surfaces of cress roots (Longman and Callow, *Physiol. Mol. Plant Pathol.,* 30:139-150, 1987; Estrada-Garcia et al., *J. Exp. Bot.* 41:693-699, 1990). Deacon and Donaldson (*Mycol. Res.,* 97:1153-1171, 1993) noted that encystment in the presence of high concentrations of attractants would be deleterious to infection potential, and thus selected against over time. They suggested, however, that attractants at the root surface may be sufficiently concentrated to predispose zoospores to encyst after contact with root surface residues.

When in contact with a root, zoospores encyst with a specific orientation so that a germ tube emerges toward the root. If zoospores encyst before contact with the root, the germ tubes will emerge in any orientation and must re-orient in order to locate the root and infect the plant. Cell surface receptors on the germ tube are thought to be involved in this root-orientation process. Morris et al. (*Plant Physiol.,* 117:1171-1178, 1998), for example, demonstrated an oriented response of *P. sojae* germling growth to low, nontoxic concentrations of isoflavonoid compounds derived from soybeans. Zentmyer (*Science,* 133:1595-1596, 1961) reported hyphal orientation of *P. cinnamomi* toward host roots, but the nature of the attractant compound(s) was not defined.

After infection, hyphae grow through plant tissue intercelluarly and/or intracellularly depending on the species of pathogen (Stossel et al., *Can. J. Bot.,* 58:2594-2601, 1980; Coffey and Wilson, in *Phytophthora: Its Biology, Taxonomy, Ecology and Pathology*, Erwin et al., eds., APS Press, 1983; Enkerli et al., *Can. J. Bot.,* 75:1493-1508, 1997; Hardham and Mitchell, *Fungal Gen. Biol.,* 24:252-284, 1998; Murdoch and Hardham, *Protoplasma,* 201:180-193, 1998). Haustoria are formed by some Phytophthora species, including *P. infestans* (Coffey and Wilson, in *Phytophthora: Its Biology, Taxonomy, Ecology and Pathology*, Erwin et al., eds., APS Press, 1983), *P. capsici* (Jones et al., *Phytopathology,* 64:1084-1090, 1974), and *P. sojae* (Stössel et al., *Can. J. Bot.,* 58:2594-2601, 1980). Both hyphae and haustoria establish close contact with host cell walls and membranes. Presumably, cell surface receptors are important in sensing plant signals, although direct evidence is lacking. Indirect evidence of cell surface receptors comes from observations such as the occurrence of vesicles in the distal portion of haustoria (Coffey and Wilson, in *Phytophthora: Its Biology, Taxonomy, Ecology and Pathology*, Erwin et al., eds., APS Press, 1983). Heath (*Can. J. Bot.,* 73(Suppl.):S131-S139, 1995) discussed the possible events of fungal hyphal tip growth involving communication with the surrounding environment via ion channel and vesicle functions.

As discussed above, evidence points to the prominence of cell surface receptors in triggering behavioral and developmental steps of Phytophthora. Cells surface receptors, therefore, may provide a means for disrupting pathogen development and so infectivity. Delay or disruption of development can have a substantial impact, since zoospores have only a limited time to locate, contact, and penetrate an infection site that is effectively moving with the growing root tip. This time limitation results from the changing susceptibility of the root tissues, since as the tissues in the elongation region mature, they become significantly less susceptible to infection (English and Mitchell, *Phytopathology,* 78:1478-1483, 1988).

"Fusion phage" are filamentous bacteriophage vectors in which foreign peptides and proteins are cloned into a phage coat gene and displayed as part of a phage coat protein. The commonly used coat genes for the production of fusion phage are the pVIII gene and the pIII gene. About 3900 copies of pVIII make up the major portion of the tubular virion protein coat. Each pVIII coat protein lies at a shallow angle to the long axis of the virion, with its C-terminus buried in the interior close to the DNA and its N-terminus exposed to the external environment. Five copies of the pIII coat protein are located at the terminal end of each virion and are involved in attachment of the phage to pIII of *E. coli* and for virus reassembly after infection and replication. Peptides displayed as part of pVIII are constrained in the matrix of their display on the virion coat. In contrast, peptides displayed as part of pIII are more flexible due to the terminal position of the pIII proteins. Specific phage can be constructed to display peptides of six to 15 amino acids in length. Insertion of random or degenerate oligonucleotides into the coat protein genes allows the production of phage displayed random peptide libraries. A typical display library contains 10 to 100 copies of as many as $10^8$ random sequence peptides. Thus, phage display is useful for screening for rare peptides with desired binding characteristics.

Phage-displayed random peptide libraries have been used for isolating ligands to cell surface receptors on mammalian cells. For example, peptides have been isolated from phage-displayed libraries that bind the transmembrane integrin glycoproteins involved in cell-extracellular matrix and cell-cell interactions (O'Neil et al, *Proteins,* 14:509-515, 1992; Smith et al., *J. Biol. Chem.,* 269:32788-32795, 1994; Healy et al., *Biochemistry,* 34:3948-3955, 1995). The phage displayed peptides specifically blocked cell adhesion to defined extracellular molecules and other cells (Koivunen et al., *J. Biol. Chem.,* 268:20205-20210, 1993; Koivunen et al., *J. Cell Biol.,* 124:373-380, 1994; Healy et al., *Biochemistry,* 34:3948-3955, 1995; Pasqualini et al., *Nature Biotech.,* 15: 542-547, 1997). Phage-displayed random peptide libraries have also been used to select peptides that distinguish between brain and kidney tissue (Pasqualini and Ruoslahti, *Nature,* 380: 364-366, 1996). In vivo, affinity-selection of phage-displayed random peptides has also been used to select peptides that bind selectively to endothelial cells of blood vessels of specific tumor tissues (Pasqualini et al., *Nature Biotech.,* 15: 542-547, 1997). When these peptides were fused to an anticancer drug and injected into tumor-bearing mice, the peptides successfully targeted the drug to tumor blood vessels and deterred progressive tumor development (Arap et al., *Science,* 279:377-380, 1998).

Phage-display methods have been applied to plant pathogens in only very limited circumstances. Phage display methods have been used almost exclusively to identify antibodies for plant virus diagnosis (Susi et al., *Phytopathology,* 88:230-233, 1998; Ziegler et al., *Phytopathology,* 88:1302-1305, 1998; Griep et al., *J. Plant Pathol.,* 105:147-156 1999; Toth et al., *Phytopathology,* 89:1015-1021, 1999). Phage display was used in a single instance to select antibodies with affinity to surface-exposed epitopes on germlings and spores of *Phytophthora infestans* (Gough et al., *J. Immunol. Methods,* 228: 97-108, 1999). Isolated phage-displayed, single-chain variable fragment (Fv) antibody fragments were not assessed for their potential to influence spore or germling behavior. Antibodies were tested for their antifungal activity with sporangia, but were found to have no detectable antifungal activity.

*Phakopsora pachyrhizi* is a fungus that causes a rust disease of soybean (*Glycines max*). The pathogen has spread from Asia to all other soybean production regions in the world. *P. pachyrhizi* arrived in the US during the fall of 2004. At present, there is no known durable resistance available in any soybean varieties. *Uromyces appendiculatus* is a fungus that causes rust on bean (*Phaseolus vulgaris*). Breeders are working to identify genes in bean that can be manipulated for rust resistance. U.S. soybean producers have anticipated the arrival of *Phakopsora pachyrhizi*, the fungus that causes soybean rust, since its reported occurrence in Brazil. The arrival of *P. pachyrhizi* in the U.S. last fall ended the anticipation, and farmers must now respond to the potential annual occurrence of this new disease. Farmer concerns have been based on reports of losses ranging from 10 to 80% in other regions of the world when control measures were not successfully implemented.

Soybean producers have been concerned because no durable, natural resistance to rust has been discovered after testing more than 18,000 US soybean varieties, and the pathogen, *P. pachyrhizi* can potentially infect any cultivar produced. In anticipation of the arrival of the rust pathogen, a great deal of research has been conducted to identify effective fungicides, and emergency governmental clearance for application to soybean has been obtained. Traditional screening and breeding methods have identified no major resistance genes to the aforementioned pathogens, and particularly in the case of *U. appendiculatus* and *P. pachyrhizi.*

Fungicides will likely be the front-line of defense for many years until new resistance genes or other forms of resistance are identified.

Fungicides have not traditionally been used in most soybean production. Consequently, there is limited information concerning the costs of this disease management practice and its likely economic viability. These concerns have led to variable estimates of the acreage in Missouri and other states that may be shifted from soybean to alternative crops.

To protect soybean farmers and to ensure that production meets national needs, alternatives to fungicides must be developed as rapidly as possible. This disclosure addresses a new type of biotechnology-based rust resistance. The technology involves the development and deployment of defense peptides in transgenic plants, such as soybeans. The technology similarly impacts the important field bean (*Phaseolus vulgaris*) rust pathogen, *Uromyces appendiculatus.*

As rust-inducing fungi, *U. appendiculatus* and *P. pachyrhizi* belong to the order Uredinales, within the class Basidiomycetes. *U. appendiculatus* produces five spore stages on a single host plant. *P. pachyrhizi* reproduces predominantly by uredospores on a single host plant. Uredospores are responsible for rapid spread of the fungus. *P. pachyrhizi* can infect dozens of legume species, in addition to soybean.

Uredospores of *U. appendiculatus* penetrate through foliar stomatal openings. *P. pachyrhizi* differs in that germinated uredospores penetrate directly through the leaf epidermal cell layer. Typically, a uredospore that lands on a leaf surface germinates to produce an infection pad (appressorium) that adheres to the surface. In both species, the appressorium produces a hyphal peg that penetrates the plant. After penetration, each fungus develops thread-like structures (hyphae) that grow inter-cellularly through leaf tissues. The hyphae enter host cells without killing them. There, they produce spherical structures (haustoria) that extract nutrients from the living leaf cells. Soon after infection each fungus forms uredia that produce additional spores.

Combinatorial phage-display libraries provide a vast array of random peptides from which to select ligands directed to proteins of interest (O'Neil et al., 1992). Phage-display peptide libraries are mixtures of filamentous phage clones, each of which displays a single foreign peptide sequence on the virion surface (Cwirla, 1990; Scott and Smith, 1990). The displayed peptide is physically linked with its coding DNA in the phage genome. Thus, the peptide can be easily and quickly identified and transferred to other vectors or display systems. Typical libraries contain $10^9$ random peptide variants.

Random peptide libraries are useful for isolating ligands of importance to cell-surface molecules of mammalian cells. For example, peptides with affinity for transmembrane glycoproteins, integrins, have been isolated from libraries by biopanning against purified molecules (O. Neil et al., 1992; Smith et al., 1994; Healy et al., 1995). Some peptides were found to block cell adhesion to defined extracellular molecules and to other cells. Effectiveness of peptide binding and inhibition was specific to peptide sequence motif (Koivunen et al., 1993; Koivunen et al., 1994; Healy et al., 1995; Pasqualini et al., 1995), and the effectiveness of selections was specific to particular organ tissues (Pasqualini and Ruoslahti, 1996).

What is needed, therefore, is a rapid and efficient method for screening peptides for specific binding to plant pathogens. Once identified, the peptides can be further evaluated for their ability to prevent infection of plants by the pathogen, and suitable peptides can be applied directly to the plant, used to treat the soil or, alternatively, sequences encoding the peptides can be introduced in the plants to confer immunity or resistance against the pathogen. In this manner, economical and environmentally safe and effective methods of controlling plant pathogens can be developed.

SUMMARY

The present invention overcomes the problems outlined above and advances the art by providing resistance to pathogens in planta. In one aspect, soybeans are made resistant to soybean rust where no durable resistance is currently available. In another example, the same general techniques may provide *Phaseoulus vulgaris* that is resistant to common rust.

In one example, a method for identifying peptides having an affinity for the surface of a plant pathogen. In this method, a library is constructed to include random peptides by providing degenerate oligonucleotides encoding peptides. The oligonucleotides are inserted into an appropriate vector that expresses the encoded peptides on its surface and is capable of transfecting a host cell. A host cell is transfected with the vector to amplify the vector in a infectious form to create a library of peptides on the vector. The vector expressing the peptide library is then contacted with a target pathogen and allowed to bind to the pathogen. Unbound vector is removed and vector that has bound to the pathogen eluted. The eluted vector is then amplified in a suitable host cell and the inserted oligonucleotides isolated. The oligonucleotides are then sequenced by any suitable method and the amino acid sequence of the peptides deduced from the sequence of the oligonucleotides.

One aspect of the disclosed instrumentalities concerns peptides, and the means for their selection, as new soybean and bean resistance factors. The peptides are advantageously identified and selected without any knowledge of specific pathogenicity targets in the pathogen. Since these peptides do not necessarily occur in soybean or bean in nature, the pathogen has not been exposed to them before. Consequently, the effectiveness of peptides deployed in soybean and bean may be broad across diverse pathogen populations, and the efficacy will likely be long lasting.

Traditional methods of phage-display peptide selection are based on panning of libraries against purified molecules of specific interest, for example as shown in Barbas et al., 2001. The present methodology differs from previous techniques in that library screening against whole-cells does not require prior knowledge of a specific target or high concentrations of the purified target molecule.

In one aspect of what is shown, small molecules known as peptides may provide rust resistance in transformed plants when displayed as part of scaffold proteins. In one example, these peptides may be selected according to the instrumentalities disclosed herein by binding affinity for infective structures of germlings, i.e., germinated spores, of *U. appendiculatus* and *P. pachyrhizi*. This binding affinity may inhibit further development and pathogenesis of the spores. The peptides are, accordingly, shown to inhibit pathogenesis of these fungi. In a particular example, cytokinin oxidase may be modified to serve as a scaffold protein for display of selected peptides in plants.

Over time, pathogen populations may be able to adapt to the presence of a selected resistance-conferring peptide. However, given the ease of peptide selection and screening, a new defense peptide can be selected rapidly to meet the challenge of changing pathogen populations. Particular advantages of the disclosed instrumentalities include speed and simplicity of peptide selection process and phenotype assessment, peptide selection does not required knowledge of pathogenicity targets in a pathogen, a high percentage of recovery of effective peptides, an ability to rapidly identify new defense peptides on demand, an ability to deploy scaffold-peptides to susceptible plant tissues, and an ability to modify scaffold-peptide constructs rapidly on demand.

Another aspect provides an antifungal composition comprising at least one peptide selected from the group consisting of ADPPRTVST (SEQ ID NO: 7), ADRPSMSPT (SEQ ID NO: 8), ADITDPMGA (SEQ ID NO: 20), AVGTHTPDS (SEQ ID NO: 21), AVSPNVHDG (SEQ ID NO: 22), LTRCLVSTEMAARRP (SEQ ID NO: 24), EFRKNYPSAAPLIPR (SEQ ID NO: 31), LFXCYPPCTYSYCLS (SEQ ID NO: 33), and AAPDLQDAM (SEQ ID NO: 4).

Still another aspect is a recombinant nucleotide comprising a sequence encoding a peptide selected from the group consisting of ADPPRTVST (SEQ ID NO: 7), ADRPSMSPT (SEQ ID NO: 8), ADITDPMGA (SEQ ID NO: 20), AVGTHTPDS (SEQ ID NO: 21), AVSPNVHDG (SEQ ID NO: 22), LTRCLVSTEMAARRP (SEQ ID NO: 24), EFRKNYPSAA- PLIPR (SEQ ID NO: 31), LFXCYPPCTYSYCLS (SEQ ID NO: 33), and AAPDLQDAM (SEQ ID NO: 4).

Yet another aspect is a recombinant vector comprising a nucleotide sequence encoding a peptide selected from the group consisting of ADPPRTVST (SEQ ID NO: 7), ADRPSMSPT (SEQ ID NO: 8), ADITDPMGA (SEQ ID NO: 20), AVGTHTPDS (SEQ ID NO: 21), AVSPNVHDG (SEQ ID NO: 22), LTRCLVSTEMAARRP (SEQ ID NO: 24), EFRKNYPSAAPLIPR (SEQ ID NO: 31), LFXCYPPCTYSYCLS (SEQ ID NO: 33), and AAPDLQDAM (SEQ ID NO: 4).

A further aspect is a cell transformed with a vector comprising a nucleotide sequence encoding a peptide selected from the group consisting of ADPPRTVST (SEQ ID NO: 7), ADRPSMSPT (SEQ ID NO: 8), ADITDPMGA (SEQ ID NO: 20), AVGTHTPDS (SEQ ID NO: 21), AVSPNVHDG (SEQ ID NO: 22), LTRCLVSTEMAARRP (SEQ ID NO: 24), EFRKNYPSAAPLIPR (SEQ ID NO: 31), LFXCYPPCTYSYCLS (SEQ ID NO: 33), and AAPDLQDAM (SEQ ID NO: 4).

In still another aspect is provided an expression cassette comprising as operatively linked components, a promoter; a nucleotide sequence encoding a peptide selected from the group consisting of ADPPRTVST (SEQ ID NO: 7), ADRPSMSPT (SEQ ID NO: 8), ADITDPMGA (SEQ ID NO: 20), AVGTHTPDS (SEQ ID NO: 21), AVSPNVHDG (SEQ ID NO: 22), LTRCLVSTEMAARRP (SEQ ID NO: 24), EFRKNYPSAAPLIPR (SEQ ID NO: 31), LFXCYPPCTYSYCLS (SEQ ID NO: 33), and AAPDLQDAM (SEQ ID NO: 4); and a transcription termination signal sequence.

An additional aspect provides, a recombinant plant comprising an expression cassette comprising a promoter; a nucleotide sequence encoding a peptide selected from the group consisting of ADPPRTVST (SEQ ID NO: 7), ADRPSMSPT (SEQ ID NO: 8), ADITDPMGA (SEQ ID NO: 20), AVGTHTPDS (SEQ ID NO: 21), AVSPNVHDG (SEQ ID NO: 22), LTRCLVSTEMAARRP (SEQ ID NO: 24), EFRKNYPSAAPLIPR (SEQ ID NO: 31), LFXCYPPCTYSYCLS (SEQ ID NO: 33), and AAPDLQDAM (SEQ ID NO: 4); and a transcription termination signal sequence.

Another aspect provides a method for characterization of peptides having an affinity for the surface of plant pathogens comprising providing a library of random peptides made by providing degenerate oligonucleotides encoding peptides; inserting the oligonucleotides into an appropriate vector that expresses the peptides on its surface and is capable of transfecting a host cell; and transfecting an appropriate host cell with the vector to amplify the vector in an infectious form to create a library of peptides on the vector. The vector expressing the peptide library is then contacted with a plant pathogen of interest and the vector allowed to bind to the pathogen. After binding, the unbound vector is removed and the bound vector eluted from the pathogen. The eluted vector is amplified in a suitable host cell and the inserted oligonucleotides in the eluted vectors isolated. The peptides encoded by the oligonucleotides are then produced, contacted with plant pathogens of interest, and the effect on infectivity observed. In one embodiment, the isolated oligonucleotides are sequenced, the amino acid sequence of the peptides deduced from the nucleotide sequence, and the peptides produced by chemical synthesis. In another embodiment, peptides are produced by inserting the isolated oligonucleotides into an expression vectors which is used to transform a suitable host cell. The transformed host cells are then maintained under conditions suitable for expression of the peptides.

Combinatorial libraries have also been screened against intact cells for recovery of peptides that bind to populations of undefined surface proteins. Peptides recovered by this type of screening can be evaluated for a phenotype of interest. For instance, we selected peptides with affinity to motile zoospores of the oomycete plant pathogen, *Phytophthora*. Phenotype screens produced a sub-collection of peptides that disrupted normal development by inducing premature encystment of the spores (Bishop-Hurley et al., 2002). We also showed that affinity-selected peptides disrupt zoospore development when displayed either in a phage-display format or when synthesized as free molecules (Laskey et al., 2001; Bishop-Hurley et al., 2002).

BRIEF DESCRIPTION OF THE DRAWINGS

These and other features, aspects, and advantages will become better understood with regard to the following description, appended claims and accompanying figures where:

FIG. 6 is a map of plasmid pJE-7. AOX-P is the alcohol oxidase promoter, Mat-α. is the mat-alpha secretory sequence, CKX1 is the cytokinin oxidase 1 sequence, Pc87 is an exemplary peptide, and AOX-TT is the alcohol oxidase termination sequence. Below the map is the double stranded sequence encoding Pc87 showing the (+) strand (5' AG CTA GCA GAT AGA CCA TCA ATG TCA CCA ACA TAG T 3', SEQ ID NO: 46) and the (−) strand (5' CT AGA CTA TGT TGG TGA CAT TGA TGG TCT ATC TGC T 3', SEQ ID NO: 47).

FIG. 7 shows the amino acid sequence (SEQ ID NO: 48) of the exemplary insert contained in pJE-7 where the underlined nucleotides are the mat-alpha secretory sequence (cleavage by the Kex2 enzyme occurs after the last underlined arginine), followed by the cytokinin oxidiase 1 sequence. The two double-underlined amino acids (KL) were added to aid in construction of the fusion protein. The amino acid sequence of the exemplary peptide Pc87 is shown in bold type.

DEFINITIONS

Figure 1:
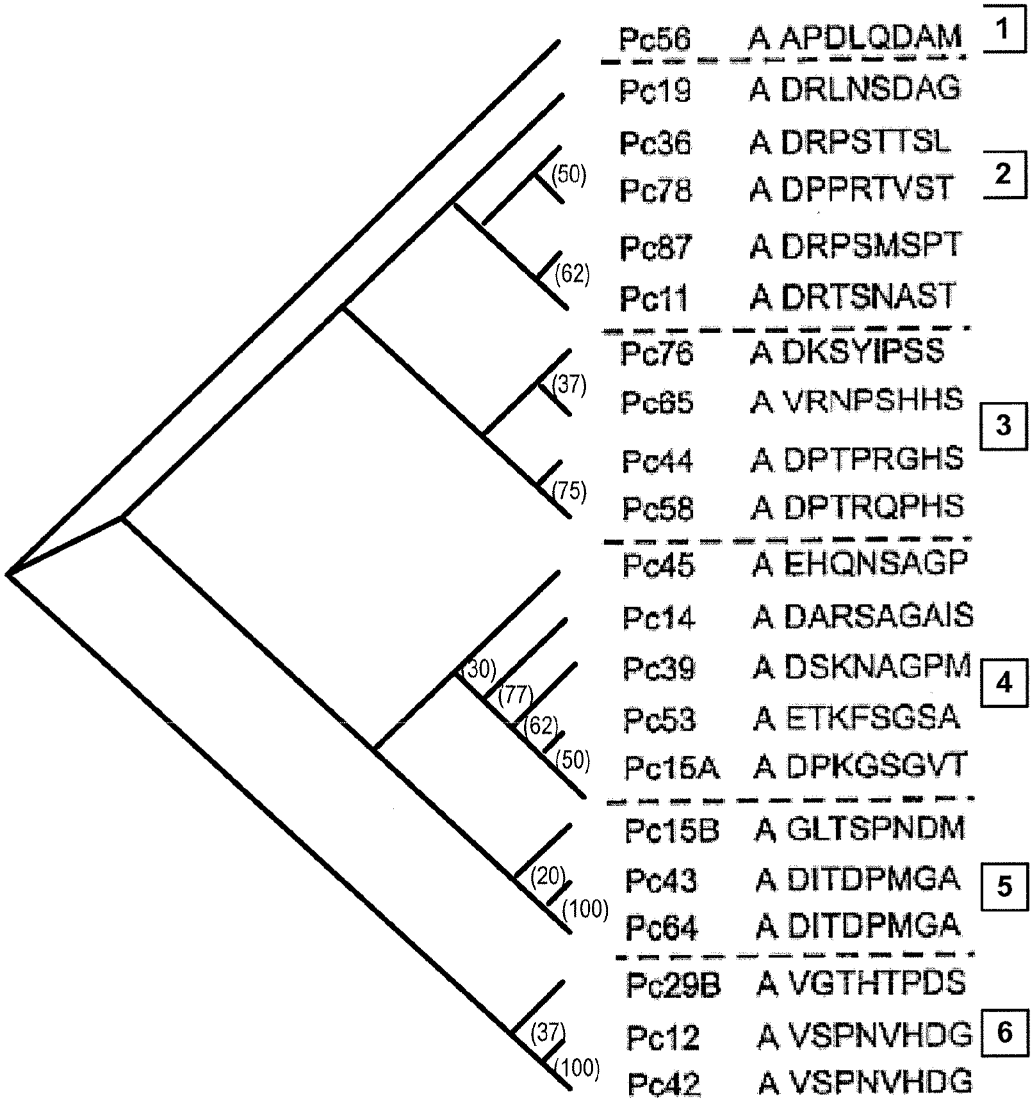
FIG. 1 shows the organization of f8 peptide sequences into six families. On the left is the dendogram and on the right are the names and sequences of the peptides.

"Secretion sequence" means a sequence that directs newly synthesized secretory or membrane proteins to and through membranes of the endoplasmic reticulum, or from the cytoplasm to the periplasm across the inner membrane of bacteria, or from the matrix of mitochondria into the inner space, or from the stroma of chloroplasts into the thylakoid. Fusion of such a sequence to a gene that is to be expressed in a heterologous host ensures secretion of the recombinant protein from the host cell.

"Germling" means a newly germinated cyst (5-8 hr post germination) that bears an emergent germ tube.

"TBS" means Tris-buffered saline (50 mM Tris-HCl, pH 7.5, 150 mM NaCl).

A "recombinant polynucleotide" means a polynucleotide that is free of one or both of the nucleotide sequences which flank the polynucleotide in the naturally-occurring genome of the organism from which the polynucleotide is derived. The term includes, for example, a polynucleotide or fragment thereof that is incorporated into a vector or expression cassette; into an autonomously replicating plasmid or virus; into the genomic DNA of a prokaryote or eukaryote; or that exists as a separate molecule independent of other polynucleotides. It also includes a recombinant polynucleotide that is part of a hybrid polynucleotide, for example, one encoding a polypeptide sequence.

"IPTG" is isopropylthiogalactoside.

"TU" means transducing unit.

"NAP buffer" is 80 mM NaCl, 50 mM $NH_4H_2PO_4$, pH adjusted to 7.0 with $NH_4OH$.

"NZY-Tc" is a bacterial growth medium containing 1% NZ amine A (a typtone-type medium; Humko-Sheffield Chemical, Norwich, N.Y.), 0.5% yeast extract, 0.5% NaCl, pH 7.0 adjusted with NaOH.

"PCR" means polymerase chain reaction.

As used herein "polynucleotide" and "oligonucleotide" are used interchangeably and refer to a polymeric (2 or more monomers) form of nucleotides of any length, either ribonucleotides or deoxyribonucleotides. Although nucleotides are usually joined by phosphodiester linkages, the term also includes polymeric nucleotides containing neutral amide backbone linkages composed of aminoethyl glycine units. This term refers only to the primary structure of the molecule. Thus, this term includes double- and single-stranded DNA and RNA. It also includes known types of modifications, for example, labels, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.), those containing pendant moieties, such as, for example, proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides include both sense and antisense strands.

"Sequence" means the linear order in which monomers occur in a polymer, for example, the order of amino acids in a polypeptide or the order of nucleotides in a polynucleotide.

"Peptide," "Protein" and "Polypeptide" are used interchangeably and mean a compound that consists of two or more amino acids that are linked by means of peptide bonds.

"Recombinant protein" means that the protein, whether comprising a native or mutant primary amino acid sequence, is obtained by expression of a gene carried by a recombinant DNA molecule in a cell other than the cell in which that gene and/or protein is naturally found. In other words, the gene is heterologous to the host in which it is expressed. It should be noted that any alteration of a gene, including the addition of a polynucleotide encoding an affinity purification moiety, makes that gene unnatural for the purposes of this definition, and thus that gene cannot be "naturally" found in any cell.

A "non-immunoglobulin peptide" means a peptide which is not an immunoglobulin, a recognized region of an immunoglobulin, or contains a region of an immunoglobulin. For example, a single chain variable region of an immunoglobulin would be excluded from this definition.

"Substantially pure" or "substantially purified" means that the substance is free from other contaminating proteins, nucleic acids, and other biologicals derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in even more preferred embodiments, at least 99% pure. The analysis may be weight or molar percentages, evaluated, e.g., by gel staining, spectrophotometry, or terminus labeling etc.

DETAILED DESCRIPTION

The following detailed description is provided to aid those skilled in the art in practicing the present instrumentalities. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

There is growing concern among soybean producers that *P. pachyrhizi*, the cause of soybean rust, will enter and spread through North American production areas in the near future. The concern arises from crop loss estimates of more than 50% in some regions of the world. Concerns about this disease have increased with the recent discovery of the rust fungus in Brazil above 5 degrees northern latitude. It is likely that in the near future, spores of *P. pachyrhizi* will be carried by prevailing winds northward into the U.S. (Rizvi, 2004). Because there are no known disease resistance genes effective against rust, current disease management plans rely upon repeated protective fungicide applications. the disclosure below provides an additional option, which is to use new peptide technologies to identify and deliver defense peptides that bind to infective structures of *P. pachyrhizi* and related rust pathogens to halt rust development. Defense peptides may be designed for expression in plants and delivered to sites of pathogen infection and colonization. Planta, such as soybean and field bean, may be engineered to express these peptides to produce plant lines that are uniquely resistant to rust.

A program of development, accordingly, identifies peptides that bind to infective *P. pachyrhizi* spores and germlings, evaluates the effectiveness of binding peptides for inhibition of spore germination and fungal growth, incorporates and tests candidate defense peptides in plants for resistance potential.

The rust pathogen produces spores (urediniospores) that infect soybean leaves, stems, and seed pods. The spores are blown by wind and land on the plant where they germinate to produce a germ tube (defined as the germling phase) that penetrates plant tissues. After penetration, the fungus develops further by producing a filamentous growth that spreads inter and intracellularly through tissues (Bonde et al., 1976; Koch and Hoppe, 1988). With time, tissue colonization leads to production of additional infective spores that are released in wind and moved to other plants.

Although some resistance genes for soybean rust are hypothesized, most have failed under field conditions or in greenhouse inoculation tests. Once the pathogen arrives in a new geographic area, growers are be faced with a situation in which there is virtually no full rust resistance available in commercial soybean cultivars or breeding lines. For the foreseeable future, growers will need to apply fungicides periodically throughout each growing season.

Discovery of new resistance genes in soybean or close relatives using conventional technologies, and the incorporation of such genes into commercial soybean lines is expected to require many years. The following disclosure advantageously expedites that process. These possibilities follow from recent advancements in peptide technology, plant transformation technology, and molecular biology, which have been combined for the advancement disclosed herein. Combinatorial peptide technology enables screening of massive, diverse collections of peptides for those which bind to infective structures of plant pathogens and disrupt their development before and during plant infection. Tools of molecular biology and plant transformation enable construction of delivery systems to express these defense peptides at sites of infection in plants.

Defense peptides may be defined as those which bind to infective structures, e.g. spores, of plant and animal pathogens to disrupt the normal development of the pathogen. Peptides that bind and disrupt or halt pathogen function achieve this effect by binding to pathogen surface proteins that are important in regulating development. A surface protein selected for this use may, for example, be an enzyme that is needed for cell wall formation and vegetative growth or perhaps, a protein that controls uptake of minerals that are critical for growth. The methods disclosed herein, by way of illustration, may effectively screen pathogens against diverse peptide collections that contain one billion or more random peptide combinations. The technique is specifically applied to defeat *P. pachyrhizi*. and related pathogens.

It will be shown by way of the following examples how to identify peptides that bind to infective *P. pachyrhizi* spores and germlings, as well as the spores of related or analogous pathogens. A collection of peptides are generated and confirmed to bind to infective spores or germ tubes (germlings) of the pathogen. To identify the binding peptides, spores or germlings are mixed with collections, conventionally known as libraries, of random peptides that are displayed on bateriophage (virus) particles, for example, as shown by Wilson et al., 1998. By this approach, spores and germlings may by way of illustration be exposed to one billion random peptides. A wide variety of many suitable peptide libraries are known to the art. In some libraries, the peptides contain only eight amino acids, while in other libraries each peptide contains 15 amino acids.

After mixing and exposure for proper incubation, washing may remove all peptides that do not stick strongly to spores and germlings. The spores and germlings may be treated to release the adhering peptides, increase their numbers, and repeat the screening process. After a plurality of repetitive screening steps where each step confirms the binding peptide binding affinity of the previous step, recovery is certain of numerous peptides that stick very strongly to proteins and other components of spore and germ tube surfaces. In one example, 3 or 4 sequential screening steps are sufficient to provide this result.

Once the peptide binding affinity is confirmed as described above, it is possible to evaluate the effectiveness of binding peptides for inhibiting spore germination and fungal growth. Once a number of binding peptides have been identified, it is possible to select those that impact pathogen function. Peptides that halt spore germination and germling growth are of particular interest. Either of these disruptive behaviors will lead to halted or reduced pathogen infection and disease. High-throughput assays may be used to test numerous peptides for ability to halt or slow spore germination or vegetative growth in *Phytophthora, P. pachyrhizi*, or analogous pathogens. Experience has shown that a large percentage of test peptides may have an impact on pathogen development.

Once a defense peptide has been identified, it is delivered to infection points within a plant, without degradation by plant enzymes. One method for achieving this delivery is to attach the peptide to a protein that is naturally produced by a plant and that is produced in tissues colonized by the pathogen. In one example, cytokinin oxidase has been used successfully for this purpose. This protein is produced naturally by plants, and it is involved in the regulation of the plant growth hormone, cytokinin. Defense peptides may be attached to this protein, and used to modify pathogen function. In one example, this has been done in *Phytophthora.*

Defense peptides may be fused to cytokinin oxidase and other proteins that are naturally secreted by cells into the intercellular space where they can come into contact with the colonizing rust pathogen. Alternatively, the fusions may include proteins that are components of plant cell walls. These proteins are also positioned to interact with the pathogen both inter- and intracellularly. Commercially available proteomic databases provide a wide variety of gene sequences for candidate peptide-carrier proteins that may be used as an alternative to CKX. These carrier protein structures may be analyzed using conventional structural proteomic algorithms for optimal presentment or display of the defense peptide.

Candidate protein-peptide constructs may be expressed and secreted initially in the yeast, *Pichia*. This host facilitates concentrating and purifying a protein or poly peptide, and testing the same for inhibition of pathogen spore germination or germling growth.

Once the best defense peptides and the best modes of display on the carrier protein are confirmed, genetic constructs may be formed for confirmation in planta, such as soybean or field bean. Methods of plant transformation and expression of foreign genes are well known in the art.

Particularly virulent and dangerous pathogens, like *P. pachyrhizi*, are contained by governmental regulation. This danger and the regulatory complexity are avoided by the use of initial peptide selection protocols using an alternative or analogous rust pathogen. *Puccinia polysora*, the fungal pathogen that causes southern rust of corn has been reported by Hollier and King, 1985. This pathogen is readily available without restrictions, and it may be handled under standard laboratory conditions.

In one embodiment peptide libraries are constructed by the insertion of nucleic acid sequences encoding peptides of six to 15 amino acids in length into suitable vectors, although sequences encoding longer peptides can be used. The peptides encoded by the nucleotides can be completely random in nature or can be constrained in their composition to meet structural or functional requirements. For example, and without limitation, a cysteine bridge can be inserted into the peptide. In one embodiment, the nucleic acid sequence does not encode an immunoglobulin (antibody) or a recognized immunoglobulin region such as a variable region. Any vector which will express the inserted oligonucleotides can be used. Preferably a vector is used which will result in expression of the peptide library on the surface of a cell or virus or on the surface of an intracellular compartment or organelle of a cell or virus. In this manner, the expressed peptides will be available to interact with potential target molecules or cells that come in contact with the surface containing the peptides. As will be apparent to one of ordinary skill in the art, if the peptides are expressed on the surface of intracellular compartments or organelles, the potential target must also reside intracellularly or the organelle or intracellular compartment must be exposed to the external environment by, for example, lysis of the cell.

Methods of producing oligonucleotides and inserting them into vectors are well known to those of ordinary skill in the art and will only be briefly reviewed herein. Most commonly, oligonucleotides are synthesized on a solid support using the phosphite triester method of Beaucage and Caruthers (*Tetrahedron Lett.* 22:1859-1862, 1981; also see, U.S. Pat. Nos. 4,973,679 and 4,458,066). Numerous solid supports are available including controlled pore glass beads, polystyrene copolymers, silica gel and cellulose paper. The preparation of an oligonucleotide begins with the linkage of the 3'-hydroxyl group of the first nucleoside to the solid support. Solid supports containing nucleotides are available from commercial sources. The oligonucleotide is synthesized from the 3' to 5' direction and the chain is elongated by nucleophilic attack of the 5'-hydroxyl of the immobilized oligonucleotide on the activated 3' phosphate or phosorphramidite of a soluble 5'-protected building block. The intermediate dinucleoside phosphite formed must next be oxidized to the more stable phosphate before chain extension. The process is repeated until the desired number of nucleotides has been added. Automated devices are commercially available for the synthesis of oligonucleotides. In addition, numerous commercial vendors provide custom oligonucleotide synthesis services.

Any vector system capable of expressing the peptides of the peptide library may be used in the practice hereof and numerous vector systems are known in the art (See e.g., Wilson and Findlay, *Can. J. Microbiol.*, 44:313-329, 1998). When the peptide is displayed as part of pVIII, suitable phage systems include type 8, type 88, and type 8+8. When pIII is utilized suitable phage systems include type 3, type 33 and type 3+3. When the peptide is inserted into pVI, suitable phage systems included type 6, type 66 and type 6+6. In addition, phage T7 and phage 8 vector systems can be used. In one preferred embodiment, the peptides of the library are expressed fused to a coat protein of a filamentous bacteriophage so that the peptides are expressed on the surface of the virion and so are available to interact with target molecules or cell surface receptors. In one preferred embodiment, the f8-1 library is used in which random 8-mer peptides are fused to the pVIII coat protein. In another preferred embodiment, the f88-4 library is used in which random 15-mer peptides are fused to the pVIII coat protein. Phage in the f88-4 library display peptides without bias toward the occurrence of any amino acid. Phage in the f8-1 library are unbiased with the exception of alanine at the first position and one of four residues at the second position. All other positions are randomly occupied by any amino acid.

Methods for production of the f8-1 phage-displayed peptide library have been described previously (See, Petrenko et al., *Prot. Engineering,* 9:797-801, 1996 and references cited therein). The library displays foreign peptides on every copy of the 3900 copies of major coat protein pVIII. Peptide expression need not be induced by IPTG. The degenerate oligonucleotide used for the 8-amino acid insert is: GCA GNN $(NNN)_7$, where N is any nucleotide. Therefore, the first amino acid is an alanine (A) and the second amino acid is a valine (V), alanine (A), aspartate (D), glutamate (E) or glycine (G). The remainder of the amino acids in the peptide are completely randomized.

Likewise, methods for the production of the f88-4 phage-displayed peptide library have also been previously described (Zhong et al., *J. Biol. Chem.* 269:24183-24188, 1994; Smith and Scott, *Methods in Enzymology,* 217:228-257, 1993; Smith, *Gene,* 128:1-2, 1993 and references cited therein). This library displays 15-amino acid foreign peptides on 150 to 300 copies of major coat protein pVIII. The remainder of the 3900 copies of the pVIII subunits are derived from the wild type pVIII. The phage genome thus bears two pVIII genes encoding two different types of pVIII molecules. One pVIII is the recombinant displaying the foreign 15-mer peptide, while the other is the wild-type pVIII normally present on the phage. Expression of the recombinant pVIII gene is driven by the IPTG inducible tac promoter/operator. Because of the presence of two pVIII genes, the f88 virion consists of a mosaic pattern of wild-type and recombinant pVIII subunits.

The oligonucleotide sequence used for the 15-mer amino acid inserts is $(NNK)_{15}$, where N is A, T, C, or G and K designates G or T. Thus, the region surrounding the 15-mer insert is: LVPMLSFA$(X)_{15}$PAEGDDPAKA (SEQ ID NO: 1), where X is any amino acid encoded by the codon NNK.

The phage particles can be used to screen the random peptides expressed on the virion for their ability to bind to compounds and cells of interest. In one preferred embodiment, the phage-displayed peptide library is used to screen for peptides that bind to plant pathogens. In another preferred embodiment the peptides are screened for their ability to bind to pathogenic fungi. In still another preferred embodiment, phage-displayed peptides are screened for their ability to bind to members of the genus Phytophthora. When examining pathogens with more than a single life stage, it is preferable that each life stage be examined, since significant differences in the number, types and affinity of binding sites can occur with changes in developmental stages.

For example, when examining members of the genus Phytophthora, approximately $10^5$ to $10^6$ organisms are mixed with approximately $10^8$ to $10^9$ phage-displayed peptides and incubated for a time sufficient to allow binding. It will be apparent to those of ordinary skill in the art that depending on factors such as the species of pathogen, the phage and the peptide, that other concentrations of organisms and displayed peptides can be used according to the present disclosure. In some cases, it may be desirable to pre-incubate the displayed peptides with other life stages of the same organism in order to identify those peptides that bind only to a specific life stage. After incubation, the organism is subject to multiple washes in order to remove unbound and weakly bound peptides. In the case of Phytophthora zoospores, washing is done using a solution of approximately 50 mM LiCl. After washing, bound phage-displayed peptides are eluted, preferably at low pH, and the eluted phage amplified in a suitable host. In one embodiment, the host is starved K91 *E. coli*. Methods for the amplification of bacteriophage in *E. coli* are well known in the art and can be found, for example, in Smith and Scott, *Methods in Enzymology,* 217:228-257, 1993; Ausubel et al. eds., *Short Protocols in Molecular Biology,* 2nd ed., Wiley & Sons, 1995; and Sambrook et al., *Molecular Cloning, Cold Spring Harbor Laboratory Press,* 1989. In one embodiment, the screening procedure is repeated at least once in order to enrich high-affinity phage displayed peptides. In another embodiment, the screening process is repeated three times.

Once phage displayed high affinity peptides are identified, the phage are amplified, preferably in *E. coli*, and the phage DNA isolated using standard methods such as those found in, for example Smith and Scott, *Methods in Enzymology,* 217:228-257, 1993; Ausubel et al. eds., *Short Protocols in Molecular Biology,* 2nd ed., Wiley & Sons, 1995; and Sambrook et al., *Molecular Cloning,* 2nd ed., Cold Spring Harbor Laboratory Press, 1989. Once the phage DNA has been isolated, the inserted oligonucleotides can be cleaved from the DNA using the same restriction enzymes used to insert the oligonucleotides, and the restriction enzyme fragments separated from the remainder of the DNA. The oligonucleotides can then be sequenced using any standard method. Sequencing can be carried out by any suitable method, for example, dideoxy sequencing (Sanger et al., *Proc. Natl. Acad. Sci. USA,* 74:5463-5467, 1977), chemical sequencing (Maxam and Gilbert, *Proc. Natl. Acad. Sci. USA,* 74:560-564, 1977) or any variation thereof, including the use of automatic sequencers. In one embodiment, sequencing is accomplished using an ABI Prism 377 automated sequencer (Applied Biosystems, Foster City, Calif.). Once the sequence of the oligonucleotides is known, the amino acid sequences of the peptides encoded can be readily deduced using the genetic code.

High-affinity binding, phage displayed peptides can be further screened for their ability to alter the development, growth and/or infectivity of pathogens. In this embodiment, phage-displayed peptides are incubated with a target pathogen for a time sufficient to allow binding. Following binding, the pathogen is observed for alterations in its development or ability to infect a host. In one embodiment, approximately 200 zoospores of a member of the genus *Phytophthora* are combined with a phage-displayed peptide in distilled water in two-fold serial dilutions at constant volume in petri dishes. The range of phage concentrations can vary, but generally ranges between 1 to $10\times10^9$ virion/μl. A negative control containing no phage is included in each screening. After an incubation period of usually about 20 minutes at room temperature, the number of zoospores encysted at each phage concentration is determined. Using this method it is possible to rationally select peptides of defined character and evaluate them for species- and life stage-specific induction of receptor-mediated functional responses, such a zoospore encystment. Peptides found to interfere with the development of a pathogen can be used to prevent or limit infection of a host with the pathogen.

The present method can also be used to characterize peptide binding receptors on the surface of plant pathogens. In this embodiment, peptide displaying phage that have been labeled (test phage) are incubated with cells of different organisms and at different stages of development. The relative binding affinity of the labeled phage can then be determined by competitive binding and. Scatchard analysis. In a competitive binding analysis, a constant concentration of test phage is allowed to bind to a target pathogen and then unlabeled challenge phage is added over a range of concentrations. The challenge phage may be the same as the test phage or it may be different. The target pathogen is then washed to remove non-specifically or weakly bound phage and the amount of test phage bound is determined by measuring the amount of label present on the target cells. The degree of competition can be measured as the concentration of challenge phage required to inhibit test phage binding by 50% ($IC_{50}$). Results from competition assays can be use to determine changes in the number, type and affinity of cell surface receptors over time.

Within the scope of the disclosed instrumentalities are recombinant oligonucleotides, discovered by the method taught herein, encoding peptides having antifungal activity. These recombinant oligonucleotides can be used to produce recombinant polynucleotides which are commonly used as cloning or expression vectors although other uses are possible. A cloning vector is a self-replicating DNA molecule that serves to transfer a DNA segment into a host cell. The three most common types of cloning vectors are bacterial plasmids, phages, and other viruses. An expression vector is a cloning vector designed so that a coding sequence inserted at a particular site will be transcribed and translated into a protein.

Both cloning and expression vectors contain nucleotide sequences that allow the vectors to replicate in one or more suitable host cells. In cloning vectors, this sequence is generally one that enables the vector to replicate independently of the host cell chromosomes, and also includes either origins of replication or autonomously replicating sequences. Various bacterial and viral origins of replication are well known to those skilled in the art and include, but are not limited to the pBR322 plasmid origin, the 2μ plasmid origin, and the SV40, polyoma, adenovirus, VSV and BPV viral origins.

The oligonucleotide sequences of the present disclosure may be used to produce antifungal peptides by the use of recombinant expression vectors containing the oligonucleotide sequence. Suitable expression vectors include chromosomal, non-chromosomal and synthetic DNA sequences, for example, SV 40 derivatives; bacterial plasmids; phage DNA; baculovirus; yeast plasmids; vectors derived from combinations of plasmids and phage DNA; and viral DNA such as vaccinia, adenovirus, fowl pox virus, and pseudorabies. In addition, any other vector that is replicable and viable in the host may be used.

The nucleotide sequence of interest may be inserted into the vector by a variety of methods. In the most common method the sequence is inserted into an appropriate restriction endonuclease site(s) using procedures commonly known to those skilled in the art and detailed in, for example, Sambrook et al., *Molecular Cloning, A Laboratory Manual,* 2nd ed., Cold Spring Harbor Press, (1989) and Ausubel et al., *Short Protocols in Molecular Biology,* 2nd ed., John Wiley & Sons (1992).

In an expression vector, the sequence of interest is operably linked to a suitable expression control sequence or promoter recognized by the host cell to direct mRNA synthesis. Promoters are untranslated sequences located generally 100 to 1000 base pairs (bp) upstream from the start codon of a structural gene that regulate the transcription and translation of nucleic acid sequences under their control. Promoters are generally classified as either inducible or constitutive. Inducible promoters are promoters that initiate increased levels of transcription from DNA under their control in response to some change in the environment, e.g. the presence or absence of a nutrient or a change in temperature. Constitutive promoters, in contrast, maintain a relatively constant level of transcription.

A nucleic acid sequence is operably linked when it is placed into a functional relationship with another nucleic acid sequence. For example, DNA for a presequence or secretory leader is operatively linked to DNA for a polypeptide if it is expressed as a preprotein which participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual,* 2nd ed., Cold Spring Harbor Press, (1989) and Ausubel et al., *Short Protocols in Molecular Biology,* 2nd ed., John Wiley & Sons (1992).

Common promoters used in expression vectors include, but are not limited to, LTR or SV40 promoter, the *E. coli* lac or trp promoters, and the phage lambda PL promoter. Useful inducible plant promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651). Other promoters known to control the expression of genes in prokaryotic or eukaryotic cells can be used and are known to those skilled in the art. Expression vectors may also contain a ribosome binding site for translation initiation, and a transcription terminator. The vector may also contain sequences useful for the amplification of gene expression.

Expression and cloning vectors can, and usually do, contain a selection gene or selection marker. Typically, this gene encodes a protein necessary for the survival or growth of the host cell transformed with the vector. Examples of suitable markers include dihydrofolate reductase (DHFR) or neomycin resistance for eukaryotic cells and tetracycline or ampicillin resistance for *E. coli*. Selection markers in plants include resistance to bleomycin, gentamycin, glyphosate, hygromycin, kanamycin, methotrexate, phleomycin, phosphinotricin, spectinomycin, streptomycin, sulfonamide and sulfonylureas. Maliga et al., *Methods in Plant Molecular Biology*, Cold Spring Harbor Press, 1995, p. 39.

In addition, expression vectors can also contain marker sequences operatively linked to a nucleotide sequence for a protein that encode an additional protein used as a marker. The result is a hybrid or fusion protein comprising two linked and different proteins. The marker protein can provide, for example, an immunological or enzymatic marker for the recombinant protein produced by the expression vector. Suitable markers include, but are not limited to, alkaline phosphatase (AP), myc, hemagglutinin (HA), β-glucuronidase (GUS), luciferase, and green fluorescent protein (GFP).

The polynucleotide sequences of the present disclosure may also be part of an expression cassette that at a minimum comprises, operably linked in the 5' to 3' direction, a regulatory sequence such as a promoter, a polynucleotide encoding a peptide of the present disclosure, and a transcriptional termination signal sequence functional in a host cell. The promoter can be of any of the types discussed herein, for example, a tissue specific promoter, a developmentally regulated promoter, an organelle specific promoter, a seed specific promoter, a plastid specific promoter, etc. The expression cassette can further comprise an operably linked targeting, transit, or secretion peptide coding region capable of directing transport of the protein produced. The expression cassette can also further comprise a nucleotide sequence encoding a selectable marker and/or a purification moiety.

More particularly, the present disclosure includes recombinant constructs comprising an isolated polynucleotide sequence encoding the antifungal peptides of the present disclosure. The constructs can include a vector, such as a plasmid or viral vector, into which the sequence has been inserted, either in the forward or reverse orientation. The recombinant construct can further comprise regulatory sequences, including, for example, a promoter operatively linked to the sequence. Large numbers of suitable vectors and promoters are known to those skilled in the art and are commercially available.

A further embodiment of the present disclosure relates to transformed host cells containing constructs comprising the oligonucleotide sequences of the present disclosure. The host cell can be a higher eukaryotic cell, such as a mammalian or plant cell, or a lower eukaryotic cell such as a yeast cell, or the host can be a prokaryotic cell such as a bacterial cell. Introduction of the construct into the host cell can be accomplished by a variety of methods including calcium phosphate transfection, DEAE-dextran mediated transfection, Polybrene, protoplast fusion, liposomes, direct microinjection into the nuclei, scrape loading, and electroporation. In plants, a variety of different methods can be employed to introduce transformation/expression vectors into plant protoplasts, cells, callus tissue, leaf discs, meristems, etc., to generate transgenic plants. These methods include, for example, *Agrobacterium*-mediated transformation, particle gun delivery, microinjection, electroporation, polyethylene glycol-mediated protoplast transformation, liposome-mediated transformation, etc. (reviewed in Potrykus (1991) *Annu. Rev. Plant Physiol. Plant Mol. Biol.* 42: 205).

Peptides produced by expression of the polynucleotides of the present disclosure can be obtained by transforming a host cell by any of the previously described methods, growing the host cell under appropriate conditions, inducing expression of the polynucleotide and isolating the protein(s) of interest. If the protein in retained within the host cell, the protein can be obtained by lysis of the host cells, while if the protein is a secreted protein, it can be isolated from the culture medium. Several methods are available for purification of proteins and are known to those of ordinary skill in the art. These include precipitation by, for example, ammonium sulfate or ethanol precipitation, acid extraction, anion or cation exchange chromatography, phosphocellulose chromatography, hydrophobic interaction chromatography, affinity chromatography, hydroxylapatite chromatography, lectin chromatography, high performance liquid chromatography (HPLC), electrophoresis under native or denaturing conditions, isoelectric focusing, and immunoprecipitation.

Alternatively, peptides encoded by the polynucleotides of the present disclosure can be produced by chemical synthesis using either solid-phase peptide synthesis or by classical solution peptide synthesis also known as liquid-phase peptide synthesis. In oligomer-supported liquid phase synthesis, the growing product is attached to a large soluble polymeric group. The product from each step of the synthesis can then be separated from unreacted reactants based on the large difference in size between the relatively large polymer-attached product and the unreacted reactants. This permits reactions to take place in homogeneous solutions, and eliminates tedious purification steps associated with traditional liquid phase synthesis. Oligomer-supported liquid phase synthesis has also been adapted to automatic liquid phase synthesis of peptides.

For solid-phase peptide synthesis, the procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent. In a common method, an amino acid is bound to a resin particle, and the peptide generated in a stepwise manner by successive additions of protected amino acids to produce a chain of amino acids. Modifications of the technique described by Merrifield are commonly used (see, e.g., Merrifield, *J. Am. Chem. Soc.* 96: 2989-93, 1964). In an automated solid-phase method, peptides are synthesized by loading the carboxy-terminal amino acid onto an organic linker (e.g., PAM, 4-oxymethylphenylacetamidomethyl), which is covalently attached to an insoluble polystyrene resin cross-linked with divinyl benzene. The terminal amine may be protected by blocking with t-butyloxycarbonyl. Hydroxyl- and carboxyl-groups are commonly protected by blocking with O-benzyl groups. Synthesis is accomplished in an automated peptide synthesizer, a number of which are commercially available. Following synthesis, the product may be removed from the resin. The blocking groups are removed typically by using hydrofluoric acid or trifluoromethyl sulfonic acid according to established methods (e.g., Bergot and McCurdy, *Applied Biosystems Bulletin,* 1987). Following cleavage and purification, a yield of approximately 60 to 70% is typically produced. Purification of the product peptides is accomplished by, for example, crystallizing the peptide from an organic solvent such as methyl-butyl ether, then dissolving in distilled water, and using dialysis (if the molecular weight of the subject peptide is greater than about 500 daltons) or reverse high-pressure liquid chromatography (e.g., using a C18 column with 0.1% trifluoroacetic acid and acetonitrile as solvents) if the molecular weight of the peptide is less than 500 daltons. Purified peptide may be lyophilized and stored in a dry state until use. Analysis of the resulting peptides may be accomplished using the common methods of analytical high pressure liquid chromatography (HPLC) and electrospray mass spectrometry (ES-MS).

In general, transgenic plants comprising cells containing polynucleotides of the present disclosure can be produced by any of the foregoing methods; selecting plant cells that have been transformed on a selective medium; regenerating plant cells that have been transformed to produce differentiated plants; and selecting a transformed plant that expresses the protein(s) encoded by the polynucleotides of the present disclosure at a desired level. Specific methods for transforming a wide variety of dicots and obtaining transgenic plants are well documented in the literature (Gasser and Fraley, *Science* 244:1293, 1989; Fisk and Dandekar, *Scientia Horticulturae* 55:5, 1993; and the references cited therein).

Successful transformation and plant regeneration have been achieved in a variety of monocots. Specific examples are as follows: *asparagus* (*Asparagus officinalis;* Bytebier et al. (1987) *Proc. Natl. Acad. Sci. USA* 84: 5345); barley (*Hordeum vulgarae;* Wan and Lemaux (1994) *Plant Physiol.* 104: 37); maize (*Zea mays;* Rhodes et al. (1988) *Science* 240: 204; Gordon-Kamm et al. (1990) *Plant Cell* 2: 603; Fromm et al. (1990) *Bio/Technology* 8: 833; Koziel et al. (1993) *Bio/Technology* 11: 194); oats (*Avena sativa;* Somers et al. (1992) *Bio/Technology* 10: 1589); orchardgrass (*Dactylis glomerata;* Horn et al. (1988) *Plant Cell Rep.* 7: 469); rice (*Oryza sativa*, including indica and japonica varieties; Toriyama et al. (1988) *Bio/Technology* 6: 10; Zhang et al. (1988) *Plant Cell Rep.* 7: 379; Luo and Wu (1988) *Plant Mol. Biol. Rep.* 6: 165; Zhang and Wu (1988) *Theor. Appl. Genet.* 76: 835; Christou et al. (1991) *Bio/Technology* 9: 957); rye (*Secale cereale*; De la Pena et al. (1987) *Nature* 325: 274); *sorghum* (*Sorghum bicolor;* Cassas et al. (1993) *Proc. Natl. Acad. Sci. USA* 90: 11212); sugar cane (*Saccharum* spp.; Bower and Birch (1992) *Plant J.* 2: 409); tall *fescue* (*Festuca arundinacea;* Wang et al. (1992) *Bio/Technology* 10: 691); turfgrass (*Agrostis palustris;* Zhong et al. (1993) *Plant Cell Rep.* 13: 1); and wheat (*Triticum aestivum;* Vasil et al. (1992) *Bio/Technology* 10: 667; Weeks et al. (1993) *Plant Physiol.* 102: 1077; Becker et al. (1994) *Plant J.* 5: 299).

In one preferred embodiment, plants are transformed with recombinant polynucleotides encoding the antifungal peptides of the present disclosure which result in the peptides being secreted by the plant. In another preferred embodiment, the antifungal peptides are secreted by the roots of the transformed plant. Plants secreting antifungal peptides can be constructed by the above described methods using expression cassettes which incorporate a secretion sequence that directs secretion of the peptides. Alternatively, plants can be transformed with a nucleotide sequence encoding a fusion protein constructed from the antifungal peptides of the present disclosure and a protein which is normally secreted by the plant. For example, a fusion protein can be produced between an antifungal peptide and the cytokinin oxidase enzyme. Cytokinin oxidase is a protective enzyme that acts to degrade exogenous cytokinins that could interfere with plant growth control. By fusing the antifungal peptides to the region of the cytokinin oxidase gene controlling secretion, the antifungal peptide would be secreted by the transformed plant, thus providing protection from pathogenic fungi.

Before being used to transform plants, fusion proteins containing antifungal peptides can be screened for activity using the phage display method of the present disclosure. In general, a fusion protein can be construction containing, an antifungal peptide; the secretory control portion of a protein, such as cytokinin oxidase; and the pVIII or pIII phage coat protein. Phage displayed fusion proteins so constructed can then be screened using the method of the present disclosure to select those fusion proteins that bind to a target pathogenic fungus and result in alternations which limit pathogenicity.

EXAMPLES

The following examples are intended to provide illustrations of the application of the present disclosure. The following examples are not intended to completely define or otherwise limit the scope of the invention.

Example 1

Fungal Species and Zoospore Production

The fungal strains used were *P. capsici* (ATCC 15399); *P. sojae* (strain 7-6-1, race 25) (A. F. Schmitthenner, Ohio State University); and *Phytophthora parasitica*. All cultures were maintained as mycelia on lima bean agar plates (*P. sojae*) or corn meal agar plates (Difco, USA) (*P. capsici* and *P. parasitica*) at 15° C. Mycelium copies were made by transferring plugs of mycelium (5 mm×5 mm) to agar plates containing clarified 10% V8® vegetable juice (Campbell Soup Co., USA). Three plugs per plate were grown for three to six days at 25° C. Sporangia production was induced in *P. capsici* by trimming the plates and incubating at 25° C. with light. After one to two days, zoospore release was induced by flooding the plates with sterile water for 20 to 30 minutes. *P. parastica* zoospore production was identical to that of *P. capsici* except that the plates were washed with sterile water for two minutes prior to incubating at 25° C. with light. Zoospore release was induced from *P. sojae* sporangia by flooding the plates four times in sterile water at 30 minute intervals. Zoospores were released within two to four hours. After their release, zoospores were filtered through four layers of cheesecloth to remove sporangial cases and mycelial fragments. A sample of the suspension was vortexed for 30 seconds to induce encystment and the cysts counted under a microscope in a hemacytometer.

Example 2

Preparation of Starved K91kan *E. Coli* Cells and Titerinz Phage as Transducing Units Prior to library screening, the phage were titered as tetracyclin transducing units (TU) in starved K91BluKan (kanomycin resistant) *Escherichia coli* cells, according to published methods (Smith & Scott, *Methods in Enzymology,* 217:228-257, 1993; Yu and Smith, *Methods in Enzymology,* 267:3-27, 1996). Transducing units are an effective way of measuring the infectivity of the phage and are usually expressed as TU/ml of phage. In brief, K91BluKan cells were grown at 37° C. with vigorous shaking (~170 rpm) in 20 ml superbroth (Smith and Scott, *Methods in Enzymology,* 217:228-257, 1993) to mid log phase ($OD_{600}$~0.45). The cells were then incubated with gentle shaking for an additional 5 minutes to allow any sheared F pIII to regenerate. The cells were centrifuged in a sterile 50 ml Oak Ridge tube at 2,200 rpm for 10 minutes in a Sorvall SS34 rotor at 4° C. The supernatant was poured off and the cells were resuspended in 20 ml of 80 mM NaCl, placed in a 125 ml culture flask and shaken gently for 45 minutes at 37° C. and 70 rpm. The cells were then centrifuged as above and resuspended in 1 ml cold NAP buffer. The starved cells were stored at 4° C. and remained infective for 3 to 5 days.

The phage were titered as transducing units (TU) in *E. coli* K91BluKan starved cells (prepared as above). Phage were analytically titered using TBS/gelatin as the diluent. Ten microliters of each phage dilution were deposited as a droplet on the inner wall of a 15 ml sterile disposable tube held at a 10° angle from the horizontal. Ten microliters of starved *E. coli* K91BluKan cells were added to each phage droplet and this was incubated for 10 minutes at room temperature to allow time for the phage to infect the concentrated cells. After 10 minutes, 1 ml of superbroth containing 0.2 mg/ml tetracyclin was added to the cells and incubated for 20 to 40 minutes at 37° C. with shaking. For amplification of the f88-4/15 mer phage, the superbroth also contained 1 mM IPTG to induce recombinant pVIII expression. The infected cells were then spread (200 ml per plate) on Luria-Bertani (LB) plates containing 40 mg/ml tetracyclin. The plates were then incubated for ~24 hr at 37° C.

Example 3

Selection of Zoospore Binding Phage

An aliquot of $10^{11}$ transducing units (TU) from the f8-1 library (Petrinko et al., *Protein Engineering,* 9:797-801, 1996) was added to $10^6$ freshly released *P. capsici* zoospores at room temperature in 4 ml of 50 mM LiCl and incubated for 30 minutes at room temperature with gentle agitation. The same procedure was used for the 188-4 library except in some cases *P. sojae* zoospores were used (Soj clones). The zoospores containing the bound phage were washed 10 times in 150 μl of 50 mM LiCl and centrifuged at 1000×g for 45 seconds to remove unbound phage. After the tenth wash, the bound phage were eluted with 200 μl of elution buffer (0.1 N HCl, glycine sufficient to bring pH to 2.2, 1 mg/ml bovine serum albumin). The eluted phage were amplified by infection of starved *E. coli* K91BluKan cells as described above. The amplified phage were then purified by precipitation with polyethylene glycol as described below, and resuspended in TBS buffer as described by Smith and Scott (*Methods in Enzymology,* 217:228-257, 1993). An aliquot of purified phage was subsequently re-applied to freshly released zoospores, as described above for a total of three affinity purifications and two amplification steps. Selective enrichment of the zoospore-binding phage was monitored by calculating the percent yield after each round of selection as described in Smith and Scott (*Methods in Enzymology,* 217:228-257, 1993). This was done by calculating the total phage (expressed as transducing units) that was applied to the zoospores and measuring the total output of phage (as transducing units) that was recovered from the zoospores and expressing the result as a percentage. The yield of phage eluted from the zoospores after each round of screening was between $10^{-4}$ to $10^{-5}$% indicating that this procedure was successful in selecting for phage binding to the zoospores. The zoospores were intact and spherical after the washing steps, showing that little or no encystment had occurred during the selection process.

Example 4

Phage Purification

*E. coli* K91BluKan cells infected with phage were grown overnight in 20 ml superbroth (containing 40 mg/ml tetracyclin) at 37° C. and 170 rpm. The culture was centrifuged to pellet the *E. coli* cells (containing phage) in a SS34 rotor for 10 min at 5,000×g. The supernatant was removed and placed in a new Oak Ridge tube and PEG/NaCl (16.7% polyethylene glycol/3.3 M NaCl) was added at a rate of 150 1 per ml supernatant to precipitate the phage. The phage were precipitated overnight at 4° C. and then pelleted by centrifugation in a 50 ml Oak Ridge tube at 10,000 rpm for 20 min in a SS34 rotor. The pelleted phage were resuspended in 1 ml of Tris-buffered saline (TBS). This was again re-precipitated by the addition of 150 ml PEG/NaCl and left overnight at 4° C. The phage were pelleted by centrifugation in a bench top centrifuge and the pellet was re-suspended in TBS.

Example 5

DNA Isolation, Sequencing and Analysis

DNA used for sequencing was isolated from individual phage clones according to the method of Smith and Scott (*Methods in Enzymology,* 217:228-257, 1993). Single-stranded DNA was sequenced from the 3' end using an ABI Prism 377 automated sequencer (Applied Biosystems, Foster City, Calif.) following the manufacturer's protocol. The primer used for f8 clones was 5'-GGAGCCTTTAATTG-TATCGG-3' (SEQ ID NO: 2). The primer used for f88 clones was 5'-AGT AGC AGA AGC CTG AAG A-3' (SEQ ID NO: 3).

DNA sequences were translated using the "translate" program of the ExPASy Molecular Biology Server (website http://www.expasv.ch/). Sequences were compared with nucleic acid and protein sequences stored in sequence databases (GenBank, EMBL, dbEST, SwissProt, PIR) using standard algorithms (i.e.) FASTA (Lipman and Person, *Science,* 227:1435-1441, 1985) and BLAST (Altschul et al., *J. Molecular Biol.,* 215:403-410, 1990) commands. Peptide sequences were aligned using ClustalW (Thompson et al., *Nuc. Acid Res.,* 22:4673-4680, 1994) with a PAM250 weight table and the dendogram viewed using TreeView (Page, *Computer Applic. Biosci.,* 12:357-358, 1996). The f8-mer DNA sequences obtained coded for 19 predicted peptide sequences (Table 1). The majority of the peptides contained amino acid residues that were predicted to be strong .alpha.-helical formers (i.e. Glu, Ala and Leu) and α-helical breakers (i.e. Gly and Pro). Despite the lack of a common motif, the ClustalW multiple sequence alignment program was used to cluster similar peptides in the form of a dendogram. The dendogram, constructed from the aligned peptides, indicated that the f8-mer peptide sequences could be grouped into six broad family groups as depicted in FIG. 1 and Table 1. Selected sequences from the f88-4/15 mer library are shown in Table 2.

Example 6

Encystment Assay

Selected phage clones were isolated according to Smith and Scott (*Methods in Enzymology,* 217:228-257, 1993), and twice purified using polyethylene glycol as described above with the exception that phage were resuspended in distilled water instead of TBS. The virion concentration was calculated by measuring the absorbance at $A_{269}$ (Smith and Scott, *Methods in Enzymology,* 217:228-257, 1993). Water droplets of approximately 20 μl containing about 400 freshly released zoospores were incubated with phage at two-fold serial dilutions so that they contained phage-bearing peptides at concentrations of either $1\times10^{10}$, $5\times10^{9}$, $2.5\times10^{9}$ or $1.25\times10^{9}$ virion/μl of droplet. A negative control received no phage and was used to monitor the amount of spontaneous encystment in the zoospore population. After a 20 minute incubation at room temperature, the number of encysted zoospores was counted using a microscope at 100× magnification. The virion concentration of phage was calculated according to Smith and Scott (*Methods in Enzymology,* 217:228-257, 1993).

Figure 2:
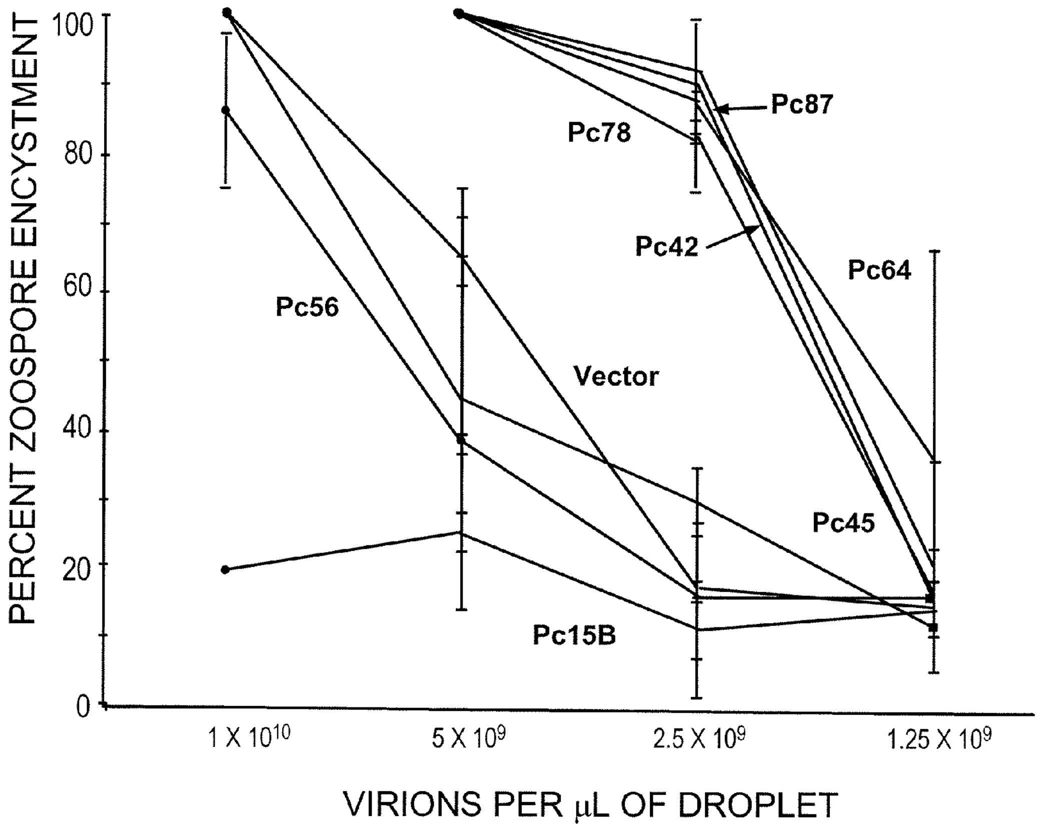
FIG. 2 shows encystment of *P. capsici* zoospores in response to contact with the indicated f8 phage-displayed peptides at the various concentrations given. Percentage values represent the means of two experiments. The percentage encystment for the control zoospore population that contained no phage varied between 0 and 10%.
Figure 3:
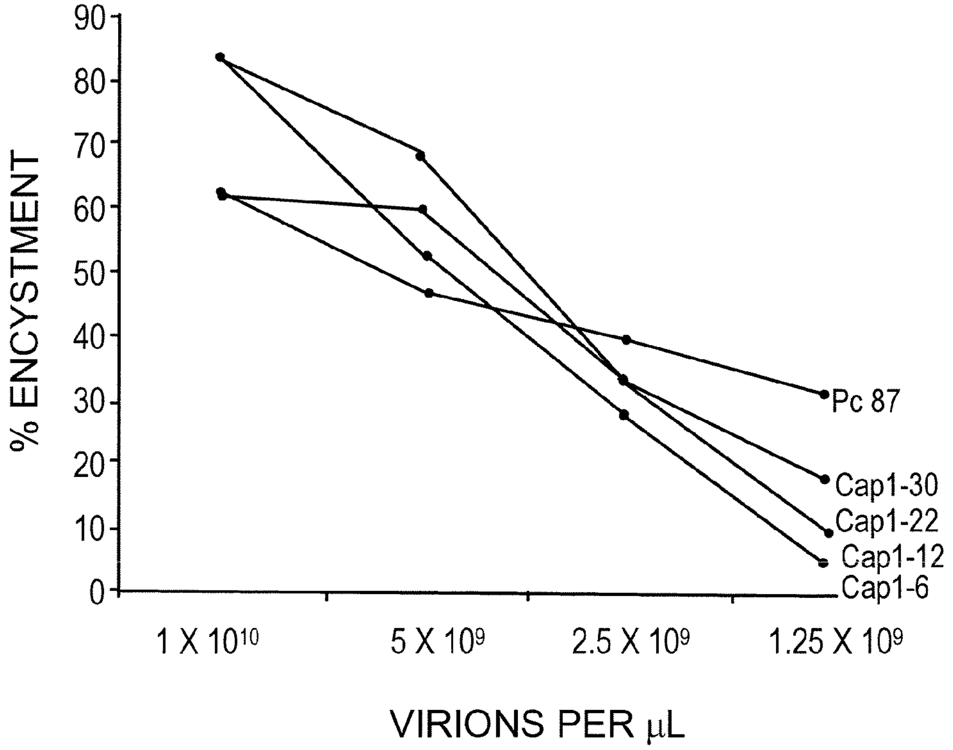
FIG. 3 shows encystment of *P. capsici* zoospores in response to contact with the indicated f8 and f88-4 phage-displayed peptides at the various concentrations given.

The effectiveness of the f8 peptides in inducing premature encystment varied with sequence family and with phage concentration (FIG. 2). At a concentration of $1\times10^{10}$ virion/μl (64 μM), many peptide families were effective in inducing encystment. At a concentration of $2.5\times10^{9}$ virion, however, there was a 3- to 5-fold difference in the peptides that caused high levels of encystment (Pc42, Pc78, Pc87 and Pc64) and peptides causing low levels of encystment (Pc15B, Pc56 and Pc45). At a concentration of $1.25\times10^{9}$ (8 μM), all peptide families were minimally effective in inducing encystment. The wild-type phage also caused encystment of the *P. capsici* zoospores; however, the fraction of zoospores encysted by the selected phage was two to seven times greater than the fraction encysted by the wild-type phage in all experiments. The ability of *P. capsici* selected, phage-bearing peptides to prematurely encyst zoospores was specific for *P. capsici*. Little or no encystment was observed when *P. sojae* and *P. parastica* zoospores were incubated with phage-bearing peptides at $1\times10^{10}$ virion/μl, a concentration that resulted in almost 100% encystment for *P. capsici* zoospores. Similar results were obtained with f88-4 15 mer peptides. The ability of representative 15 mer peptides to cause premature encystment in comparison to the f-8 clone Pc87 is shown in FIG. 3.

Example 7

Binding Specificity

Phage-displayed peptides with high and low encystment induction abilities were compared for their ability to bind to *P. capsici* zoospores. Phage clones Pc87 and Pc45 were randomly selected as the representative clones that induced high and low levels of encystment, respectively (cf. FIG. 2). Phage vector was included as a control treatment. Phage clones were amplified by *E. coli* infections and purified as described above. For each binding reaction, $5\times10^{10}$ TU of phage were incubated with 200,000 *P. capsici* zoospores. The binding reaction and washes were performed as described in Example 3 for phage selection. Phage eluted from the zoospore population were titered in *E. coli* K91BluKan cells and expressed as total transducing units. A similar procedure was used to determine whether the selected phage bound to *P. capsici* cysts.

Figure 4:
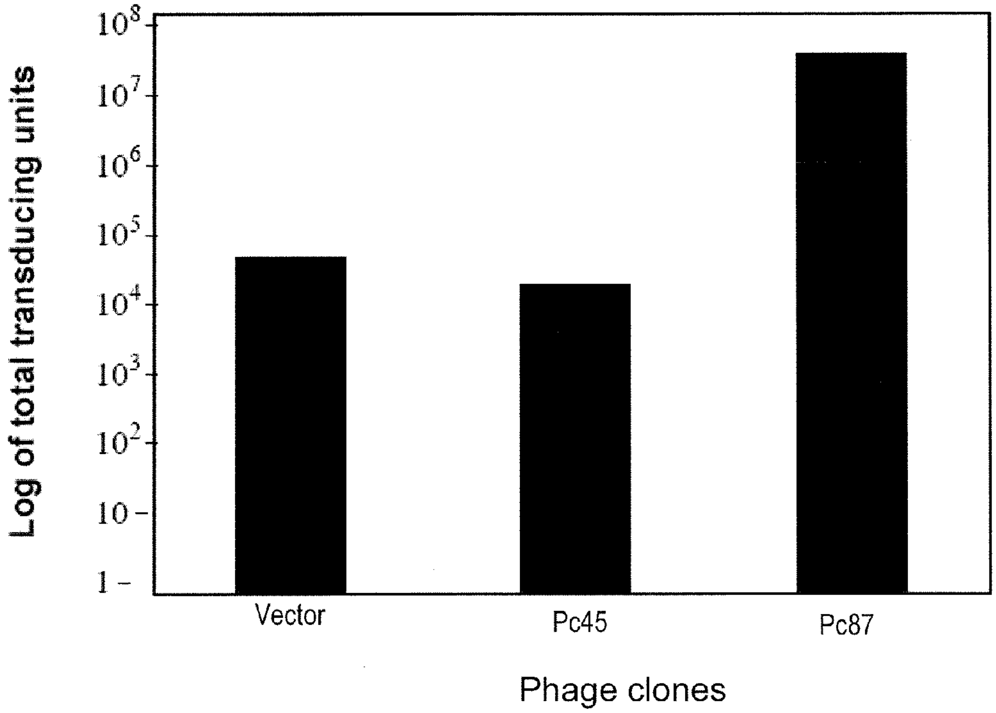
FIG. 4 shows binding of the indicated phage-displayed peptides to *P. capici* zoospsores. Values represent the mean of three experiments.
Figure 5:
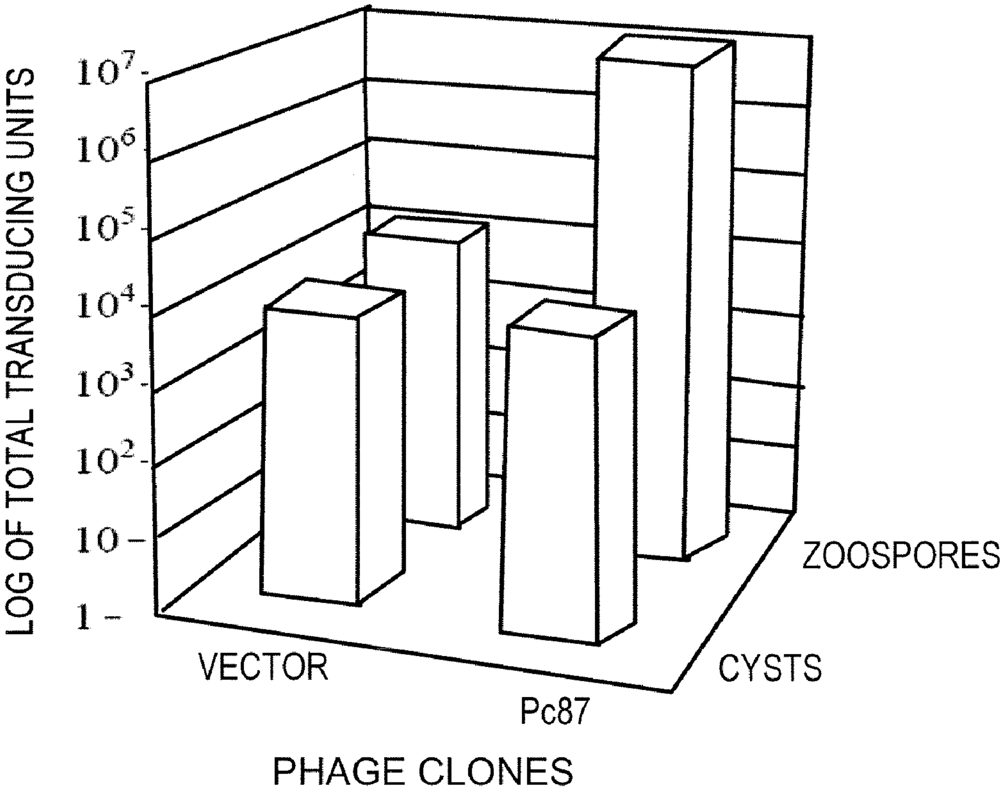
FIG. 5 shows the binding specificity of the indicated phage-displayed peptides to *P. capici*. Values represent the mean of three experiments.

Phage vector and clones Pc45 and Pc87 bound differentially to *P. capsici* zoospores. More than $10^{7}$ TU of phage Pc87 were eluted from zoospores after 30 minutes incubation, while only about 50,000 TU of phage Pc45 or phage vector were eluted under the same conditions (FIG. 4). Moreover, binding was specific for the zoospore stage: less than $10^{4}$ Pc87 TU were eluted from cysts-about the same background binding observed with control vector phage (FIG. 5).

Example 8

Construction of Secreted Fusion Protein

Carboxy-terminal DNA fusions were constructed to encode for the peptides of interest by ligation of synthetic oligonucleotides into the restriction enzyme sites, HindIII and XbaI, of the carrier vector pJE-6. The plasmid vector pJE-6 was constructed from the *Pichia pastoris* expression construct pROM-46 derived from the plasmid pPICZ-alpha (Invitrogen, Carlsbad, Calif.), previously described (Cregg et al., *Bio/Technology,* 11:905-910, 1993; Rosenfeld, *Methods in Enzymology,* 306:154-169, 1999). Plasmid pROM-46 was digested with restriction endonuclease, HindIII, filled-in with Klenow enzyme and dNTP's, and re-ligated withT4 DNA ligase. These steps eliminated a HindIII restriction site present within the pPICZ-alpha plasmid sequence, and the plasmid was designated pJE-4. The sequence at the 3' end of the coding sequence was mutagenized by PCR to replace the stop codon with the restriction site HindIII. This plasmid was designated pJE-6. Synthetic oligonucleotides encoding for an exemplary peptide (Pc87, ADRPSMSPT, SEQ ID NO: 8), were ligated into the plasmid pJE-6, digested with HindIII and XbaI. This plasmid designated pJE-7 (FIG. 6). The pJE-7 plasmid was sequenced to confirm the insert and the results are in shown in FIG. 7.

TABLE 1

| FAMILY | CLONE | AMINO ACID SEQUENCE | SEQ ID NO |
|---|---|---|---|
| 1 | Pc56 | AAPDLQDAM | 4 |
| 2A | Pc19 | ADRLNSDAG | 5 |
| | Pc36 | ADRPSTTSL | 6 |
| | Pc78 | ADPPRTVST | 7 |
| | Pc87 | ADRPSMSPT | 8 |
| | Pc11 | ADRTSNAST | 9 |
| 2B | Pc76 | ADKSYIPSS | 10 |
| | Pc65 | AVRNPSHHS | 11 |
| | Pc44 | ADPTPRGHS | 12 |
| | Pc58 | ADPTRQPHS | 13 |
| 3A | Pc45 | AEHQNSAGP | 14 |
| | Pc14 | ADARSAGAIS | 15 |
| | Pc39 | ADSKNAGPM | 16 |
| | Pc53 | AETKFSGSA | 17 |
| | Pc15A | ADPKGSGVT | 18 |
| 3B | Pc15B | AGLTSPNDM | 19 |
| | Pc43/PC64 | ADITDPMGA | 20 |
| 4 | PC29B | AVGTHTPDS | 21 |
| | Pc12/Pc42 | AVSPNVHDG | 22 |

TABLE 2

| CLONE | AMINO ACID SEQUENCE | SEQ ID NO. |
|---|---|---|
| Cap1/18 | VAAFSLVWATHLMLS | 23 |
| Cap1/12 | LTRCLVSTEMAARRP | 24 |
| Cap1/9 | SAPYLPYFDLLHFPI | 25 |
| Cap1/13 | PSSYEASRRPEHWXF | 26 |
| Cap1/11 | SATDTTLPMMTAIRS | 27 |
| Cap1/22 | TRLSPMESXAMLLAP | 28 |
| Cap1/20 | LLPVSPPFAPNASST | 29 |
| Cap1/24 | MSNFPTSHAPCPVEI | 30 |
| Cap1/6 | EFRKNYPSAAPLIPR | 31 |
| Cap1/23 | PXVHGSIPLTPPLGF | 32 |
| Cap1/30 | LFXCYPPCTYSYCLS | 33 |
| Cap1/1 | MSNFPTSHAPCPVXI | 34 |
| Cap1/16 | PEWKSSWSPCTPRCP | 35 |
| Cap1/28 | AMSRWLRPRE(M/I)NAPP | 36 |
| Cap1/19 | THTTFXVTVXLHEPP | 37 |
| Cap1/27 | MTSPRNSQLIVPFCL | 38 |
| Cap1/7 | PTLGRFNRPSCSIIV | 39 |
| Soj2-2 | APQCHPHLPFDMIHV | 40 |
| Soj2-3 | NHNSLPAQYLVXILR | 41 |
| Soj2-4; Soj2-6 | DQPCTPSPDVSFYRS | 42 |
| Soj2-8 | VAAPSHWLKPSLDCF | 43 |
| Soj2-9 | NPLYKNPPPRVAMCL | 44 |
| Soj2-19 | LIFRYAPPPLFLRPP | 45 |

As shown above, protein scaffolds may be designed for display of peptides when the peptides are transformed into plants. By way of illustration, cytokinin oxidase (CKX) may be used as a peptide-delivery scaffold. A member of the CKX family derived from maize (Morris, 1997) may, for example, be used as a delivery molecule. CKX is endogenously produced, possesses a peptide signal sequence for secretion from cells and is sufficiently glycosolated to provide stability in the presence of proteolytic enzymes in the intercellular region (Morris et al., 1999).

Figure 9:
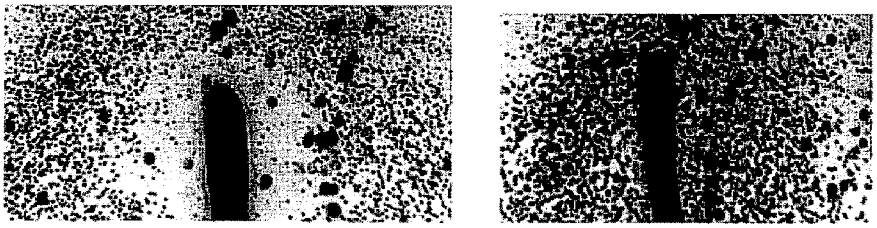
FIG. 9 shows encystment of zoospores around the apical region of a transformed root secreting cytokinin oxidase (CKX) that displays an affinity-selected selected peptide (left) and normal zoospore encystment pattern around a wild-type root tip (right).

Based on the known three-dimensional structure of CKX, as reported by Malito et al., 2004, CKX may be engineered to display peptides at an exposed C-terminus. The scaffold constructs ay, for example, be expressed and secreted from yeast. In initial experiments the inhibitory ability of selected peptides was dramatic, and 80-90% zoospore encystment was obtained. In water controls, *Phytophthora* zoospore encystment was 25% or less (Fang et al., 2004). Tomato hairy roots may, for example, be produced using these constructs, and in doing so it was found that the scaffold-peptides are secreted into the rhizosphere where they induce zoospore encystment before they accumulate at the root surface, thus blocking infection. This is shown in FIG. 9.

Figure 10:
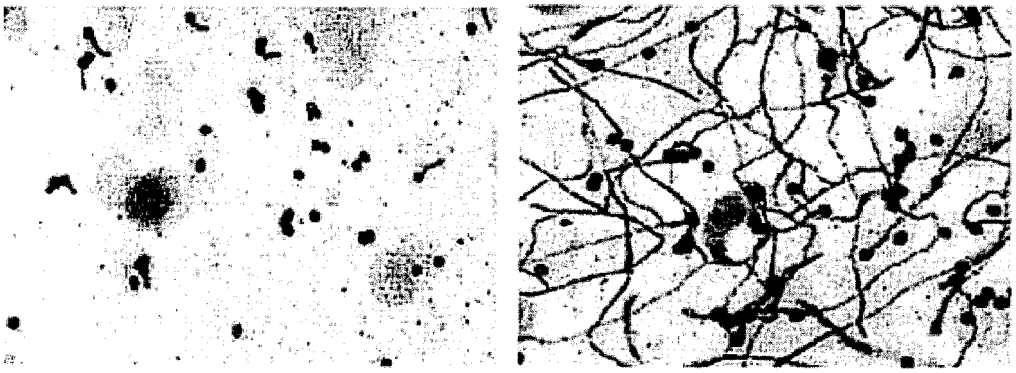
FIG. 10 shows inhibition of *U. appendiculatus* gemiling growth by affinity-selected phage-peptide clone 19 (left), and normal uredospore germination and growth in the presence of non-selected phage library (right).

In addition to the above work but by expansion of the same techniques, 15-mer peptides were selected from combinatorial libraries that bind strongly to uredospores of *U. appendiculatus*. This fungus was used as a surrogate or selected analog for *P. pachyrhizi*, where access to *P. pachyrhizi* is closely controlled for containment of this pathogen. These screens identified a number of peptides that inhibit growth after initial spore germination, for example, as shown in FIG. 10. The peptides are effective at micromolar concentrations. Deployment of defense peptides in CKX may enable delivery to the surface of fungal hyphae that penetrate the intercellular space of leaves.

Example 9

Peptide Selection Methodology

Figure 8:
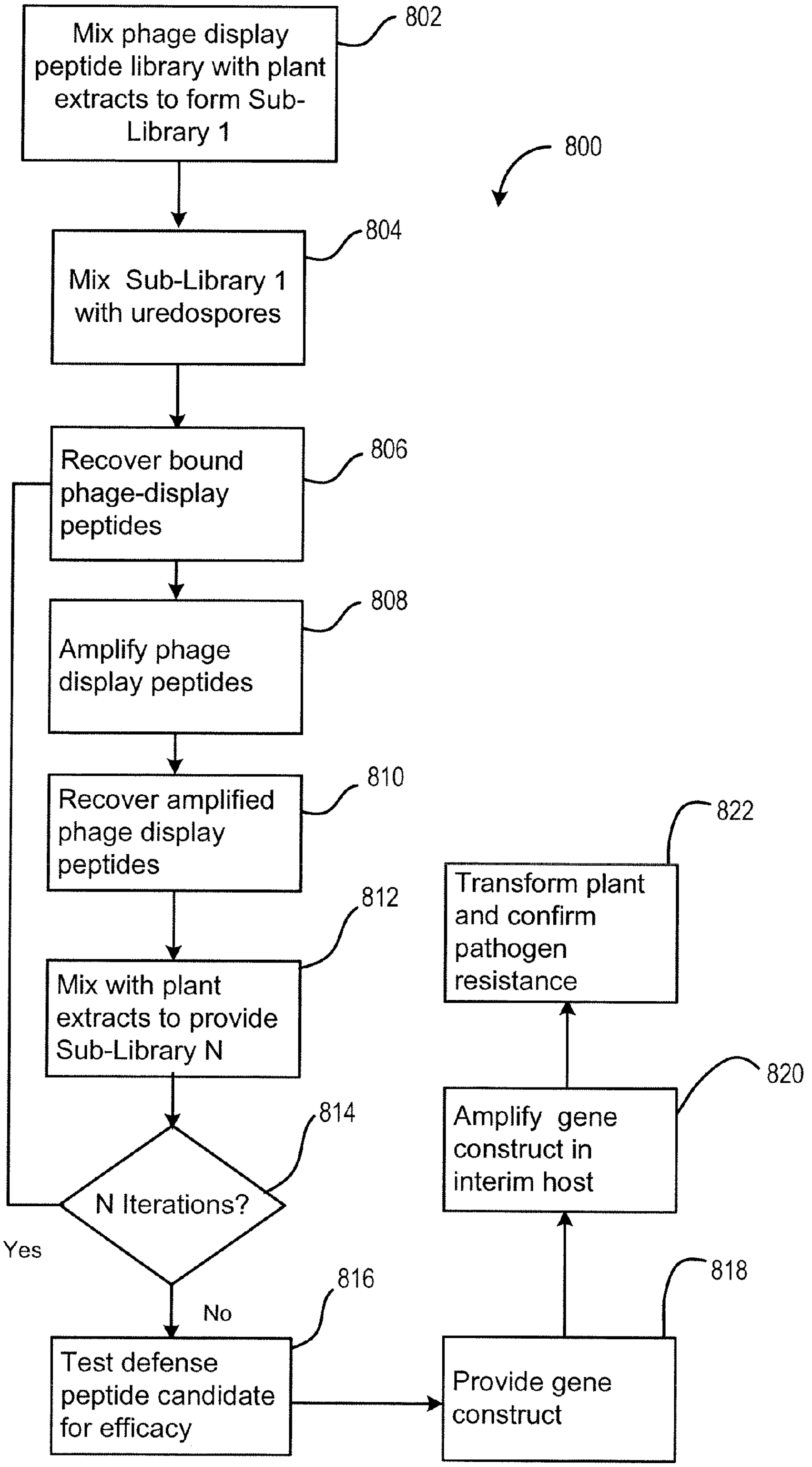
FIG. 8 is a process schematic diagram showing one method for identifying plant defense peptides that may be used to transform planta and impart resistance to rust pathogens.

FIG. 8 is a process schematic diagram showing a protocol 800 for peptide selection. To begin, a starting phage-display peptide library may be mixed in step 802 with plant extracts to remove peptides that interact with plant proteins and other factors. The output with such peptides removed is designated Sub-library 1.

Sub-library 1 is mixed 804 with germinated uredospores or germlings by what is commonly known as a biopanning technique. Bound phage-display peptides are recovered 806 from the germlings. The concentration of each recovered phage-display peptide is increased by amplification 808 in *E. coli*. The phage-display peptides are recovered 810 after amplification and mixed 812 with plant extracts to again ensure removal of peptides that interact with plant proteins and other factors. The output with such peptides removed is designated Sub-library 2.

Step 814 determines whether the above steps have been performed a sufficient number of times to assure stringency of selection of candidate plant defense peptides. Commencing with Sub-library 2, Sub-libraries 3, 4 and 5 are generated by successive iterations n in which steps 806 through 812 are repeated. Each iteration entails mixing the most recently generated Sub-library, e.g., Sub-library 2, with germinated uredospores or germlings in with use of the biopanning technique. Bound phage-display peptides are recovered from the germlings. The concentration of each recovered phage-display peptide is increased by amplification in *E. coli*.

Once the process has iterated n times, according to process design, randomly selected phage clones from Sub-library n (or from any other of n Sub-libraries) may be tested 816 for their ability to inhibit growth of germlings, i.e., germinated uredospores. Candidate peptides that show successful inhibition may be provided 818 as fused gene constructs combining the plant defense peptides with a plant surface protein gene, such as CKX, amplified 820 in an interim host, such as *Pichia*, and eventually used to transform 822 soybean or field bean to impart rust resistance.

A specific embodiment of the foregoing method may be described in context of five parts, A through E.

Part A entails the preparation of Sub-library 1 by removal of peptides that interact with plant components. A 3.0 g quantity of Pinto leaf is mixed with 7 ml of buffer (20 mM Tris-HCl, 5 mM EDTA, pH 7.0) and the mixture is ground to provide a homogenate. In a 2 ml micro tube, 0.9 ml of the homogenate is combined with 0.1 ml of $10^{14}$ phage (f88-4/15-mer), to provide a total of $10^{13}$ virions. The resulting mixture is incubated at room temperature of about 23° C. for 30 minutes on an orbital shaker (~500 rpm). The incubated mixture is centrifuged using a conventional centrifuge at top speed for 5 minutes. The supernatant is recovered, saved, and centrifuged again. The supernatant is used for phage amplification.

Part B involves a first round of biopanning. A approximately 1.5 million spores from a selected pathogen are incubated in 0.01% Tween 20 and 25 ppm B-ionone for 5 hours at 20 C. Add $10^{12}$ TU phages. The mixture is divided into 2 microtubes totaling 3 ml in volume. The microtubes including the spore/phage mixture are incubated at room temperature of about 23° C.) on an orbital shaker (~500 rpm) for 30 minutes. The incubated mixture is centrifuged, supernatant is removed, 0.5 ml of water is added, and the remaining contents are combined into one micro tube. The combined materials are centrifuged, supernatant is removed, and the pellet is washed with 1 ml of water. This step of centrifugation with removal of supernatant and washing is repeated ten times. A 150 ul quantity of elution buffer is added to the pellet, which contains phage and spore. The elution buffer is mixed well and the mixture stands for 5 minutes at room temperature. The mixture is then centrifuged and the supernatant is saved. A 75 ul of elution buffer is added and mixed for additional centrifugation as before. All of the supernatant is combined. This is repeated using 210 ul of elution buffer. A 44 ul quantity of 1 M Tris-HCl (pH 9.0) is added to neutralize the eluted supernatant. The neutralized supernatant is amplified top produce Sub-library 1.

Part C entails the preparation of Sub-library 2. Sub-library 2 is produced using the amplified Sub-library 1 from the first round of biopanniing in Part B. This is done by using Sub-library 1 instead of original f88-4/15-mer library of Part A, but otherwise following Part A of the protocol.

Part D entails the generation of additional Sub-libraries by use of further rounds of biopanning including rounds 2, 3 and 4. Part B is repeated three times:

1. For biopanning round 2, $4.2\times10^{11}$ TU phages from the $2^{nd}$ Sub-library are used to produce Sub-library 3;
2. For biopanning round 3, $5.6\times10^{11}$ TU phages amplified from the 2nd biopanning are used to produce Sub-library 4; and
3. For biopanning round 4, $5.1\times10^{11}$ TU phages amplified from the 3rd biopanning are used to produce Sub-library 5.

Colonies from biopanning-round 4 are picked, sequenced, and tested for inhibition of germling growth.

Part E entails testing for inhibition of uredospore growth. Incubate 30 ul of germinated spores (~250) with $3\times10^{12}$ at 20 C overnight. Assess fungal germ tube growth (i.e. germling growth) and compare with water and f88, i.e. phage only without any display peptide, as controls.

Example 10

Peptides that Inhibit Growth of *Uromyces Appendiculatus* and by Blocking Germling (Germinated Spore) Development The methodology of Example 9 may be repeated for the pathogens *U. appendiculatus*. Tables 3 and 4 show peptides that may be used to inhibit growth of germinated uredospores (germlings) from these pathogens.

TABLE 3

Peptides showing strong growth inhibition of *U. appendiculatus*:

| Phage-peptide clone | Sequence | SEQ ID NO: |
|---|---|---|
| Pp 15 | ADPCHMPPRMPPLPI | 49 |
| Pp 19 | NHVSTLKTRHRLIPF | 50 |
| Pp 18 | SSNAPPLSYPPLLVP | 51 |
| Pp 31 | TMARPIPTFLPPPSL | 52 |
| Pp 6 | TVAPTTHRHYVWSMD | 53 |
| Pp 16 | VFTPMNLSPPFMQPP | 54 |

TABLE 4

Peptides showing medium growth inhibition of *U. appendiculatus*:

| Phage-peptide clone | Sequence | SEQ ID NO: |
|---|---|---|
| Pp 55 | AAGPNIPPPHRASTW | 55 |
| Pp 28 | AHLYSGASLYRVYRS | 56 |
| Pp 56 | GPPSILLAIGTLSLT | 57 |
| Pp 50 | LSSPYACALFVVKGA | 58 |
| Pp 39 | RGWSVSHHSLLMPVP | 59 |
| Pp 21 | RSTASPQALNPLVAS | 60 |
| Pp 53 | SLFFEVSRMLVRLLS | 61 |
| Pp 2 | SRWWRCVTMTQPCTT | 62 |
| Pp 37 | VVALRWGWSPLRPPG | 63 |

Example 11

Use of cytokinin oxidase as a protein scaffold for delivery of select peptides to points of *U. appendiculatus* infection of bean (*Phaseolus vulgaris*) tissues.

CKX is modified as described above to fuse the defense peptides of Tables 3 and 4. An *agrobacterium*-mediated transformation of *Phaseolus vulgaris* is performed to provide a plant expressing each peptide. The transformed plants are exposed to *U. appendiculatus*. The rate and severity of infection are compared to a control plant to confirm efficacy of the defense peptides against the pathogen.

Example 12

Use of Cytokinin Oxidase as a Protein Scaffold for Delivery of Select Peptides to Points of *P. Pachyrhizi*. Infection of Soybean (*Glycine Max*) Tissues CKX is modified as described above to fuse the defense peptides of Tables 3 and 4. An agrobacterium-mediated transformation of soybean is performed to provide a plant expressing each peptide. The transformed plants are exposed to *P. pachyrhizi*. The rate and severity of infection are compared to a control plant to confirm efficacy of the defense peptides against the pathogen.

CONCLUSION

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

REFERENCES

The following documents are hereby incorporated by reference the same extent as though fully disclosed herein:

Barbas, C. F., III. Burton, D. R., Scott, J. K., Sliverman, G. J. (2001). Phage Display. A Laboratory Manual. Cold Spring harbor Laboratory Press.

Bishop-Hurley, S. L., Schmidt, F. J., Erwin, A. L., and Smith, A. L. (2005). Peptides Selected for Binding to a Virulent Strain of Haemophilus influenzae by Phage Display Are Bactericidal. Antimicrob. Agents Chemother. 49 2972-2978.

Bishop-Hurley, S., Schmidt, F. J., Smith, G. P., Morris, R. O., Elder, J., Roop, P., and English, J. T. 2002. Phage display peptides that disrupt life-stage progression in *Phytophthora*. App. Env. Micro. 68:3315-3320.

Bonde, M. R., Melching, J. S., and Bromfield, K. R. 1976. Histology of the suscept-pathogen relationship between *Glycine* max and *Phakopsora pachyrhizi*, the cause of soybean rust. Phytopathology 66:1290-1294.

Cwirla, S. E., Peters, E. A., Barrett, R. W., and Dower, W. J. (1990). Peptides on phage: a vast library of peptides for identifying ligands. Proc. Natl. Acad. Sci. 87:6378-6382.

Fang, Z, Mounter, S. Simon, M., Schmidt, F. J., and English, J. T. (2004). Protein scaffold design for delivery of peptides that induce encystment of *Phytophthora capsici* zoospores. Abstract presented at the NSF *Phytophthora* Molecular Genetics Workshop. New Orleans, La.

Healy, J. M., Murayama, O., Maeda, T., Yoshino, K., Sekiguchi, K., and Kikuchi, M. (1995). Peptide ligands for integrin V3 selected from random phage display libraries. Biochemistry 34:3948-3955.

Hollier, C. A., and King. S. B. 1985. Effects of temperature and relative humidity on germinability and infectivity of *Puccinia polysora* uredospores. Plant Dis. 69:937-939.

Koch, E., and Hoppe, H. H. 1988. Development of infection structures by the direct-penetrating soybean rust fungus (*Phakopsora pachyrhizi* Syd.) On artificial membranes. J. Phytopathol. 122:232-244.

Koivunen, E., Gay, D. A., Ruoslahti, E. (1993). Selection of peptides binding to the 51 integrin from phage display library. J. Biol. Chem. 268:20205-20210

Koivunen, E., Wang, B., and Ruoslahti, E. (1994). Isolation of a highly specific ligand for the 51 integrin from phage display library. J. Cell Biol. 124:373-380.

Laskey, J. T., Bishop-Hurley, S., Mounter, S. A., English, J. T., and Schmidt, F. J. (200). Phage-display peptides that disrupt developmental progression of Phytophthora species. Phytopathology 91: S53.

Morris, R. O. 1997. Hormonal regulation of seed development. pp 117-149 in: Larkins, B. A., and Vasil, I. K., eds. Cellular and Molecular Biology of Plant Seed Development. Kluwer Academic Publ., Boston.

Morris R. O., Bilyeu K. D., Laskey J. G., Cheikh N. N. (1999) Isolation of a gene encoding a glycosylated cytokinin oxidase from maize. Biochemical & Biophysical Research Communications 255: 328-333

O'Neil, K. T., Hoess, R. H., Jackson. S. A., Ramachandran, N. S., Mousa, S. A., and DeGrado, W. F. (1992). Identification of novel peptide antagonists for GPIIb/IIIa from a conformationally constrained phage display library. Proteins 14:509-515.

Pasqualini, R., Koivunen, E., Ruoslahti, E. (1995). A peptide isolated from phage display libraries is a structural mimic of an RGE-binding site on integrins. J. Cell Biol. 130: 1189-1196.

Pasqualini, R., and Ruoslahti, E. 1996. Organ targeting in vivo using phage display peptide libraries. Nature. 380: 364-366.

Rizvi, A. 2004. Soybean Rust Colloquium, Annual Meeting of the Southern Soybean Disease Workers, St. Louis, Mo.

Scott, J. K., and Smith, G. P. (1990). Searching for peptide ligands with an epitope library. Science 249:386-390.

Smith, J. W., Hu, D., Satterthwait, A., Pinz-Sweeney, S., and Barbas III, C. F. (1994). Building synthetic antibodies as adhesive ligands for integrins. J. Biol. Chem. 269:32788-32795.

Wilson, D. R., and Finlay, B. B. 1998. Phage display: applications, innovations, and issues in phage and host biology. Can. J. Microbiol. 44:313-329.

What is claimed is:

1. An isolated polynucleotide comprising a first sequence encoding a plant defense peptide selected from the group consisting of SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, and combinations thereof.

2. The polynucleotide of claim 1, further comprising a second sequence encoding a second polypeptide attached to said plant defense peptide, wherein said second polypeptide facilitates the presentment of the plant defense peptide to a plant pathogen.

3. The polynucleotide of claim 2, wherein the second polypeptide is a cytokinin oxidase (CKX).

4. A vector comprising the polynucleotide of claim 1.

5. A cell comprising the polynucleotide of claim 1.

6. A plant comprising the polynucleotide of claim 1.

7. The plant of claim 6, wherein the polynucleotide is introduced into said plant by transformation.

8. The plant of claim 6, wherein the plant is a soybean plant.

9. The plant of claim 6, wherein the polynucleotide further comprises a second coding sequence encoding a peptide delivery scaffold, wherein the expression of said peptide-delivery scaffold facilitates the delivery and/or display of said plant defense peptide on the surface of the cells of the plant.

10. The plant of claim 9, wherein the first sequence encodes the peptide of SEQ ID NO: 50.

11. The plant of claim 9, wherein said peptide-delivery scaffold is a maize cytokinin oxidase.

12. The plant of claim 6, wherein said plant is resistant to infection caused by at least one fungus belonging to the genus *Phytophthora*.

13. The plant of claim 6, wherein said plant is resistant to infection caused by at least one fungus selected from the group consisting of *Uromyces appendiculatus, Phytophthora capsici*, and *Phakopsora pachyrhizi*.

14. A plant comprising the polynucleotide of claim 3.

* * * * *